(12) United States Patent
Fateh

(10) Patent No.: US 10,304,314 B2
(45) Date of Patent: May 28, 2019

(54) METHOD OF AND APPARATUS FOR TARGETED INTERACTIVE HEALTH STATUS NOTIFICATION AND CONFIRMATION

(71) Applicant: KALI CARE, INC., Mountain View, CA (US)

(72) Inventor: Sina Fateh, Mountain View, CA (US)

(73) Assignee: KALI CARE, INC., Mountain View, CA (US)

( * ) Notice: Subject to any disclaimer, the term of this patent is extended or adjusted under 35 U.S.C. 154(b) by 946 days.

(21) Appl. No.: 14/530,294

(22) Filed: Oct. 31, 2014

(65) Prior Publication Data

US 2015/0120320 A1 Apr. 30, 2015

Related U.S. Application Data

(60) Provisional application No. 61/898,439, filed on Oct. 31, 2013.

(51) Int. Cl.
*G06Q 50/22* (2018.01)
*G08B 21/24* (2006.01)

(52) U.S. Cl.
CPC ............ *G08B 21/24* (2013.01); *G06Q 50/22* (2013.01)

(58) Field of Classification Search
CPC ............ A61B 5/681; A61B 2562/0219; A61B 5/0022; G06F 19/3418; G08B 21/24; G06Q 50/22
USPC .......................................... 705/2–3
See application file for complete search history.

(56) References Cited

U.S. PATENT DOCUMENTS

| | | | |
|---|---|---|---|
| 2004/0156554 A1* | 8/2004 | McIntyre | G06T 5/00 382/254 |
| 2006/0058619 A1* | 3/2006 | DeYoe | G06T 11/00 600/407 |
| 2009/0076423 A1 | 3/2009 | Reeves et al. | |
| 2010/0056873 A1* | 3/2010 | Allen | A61B 5/01 600/300 |
| 2012/0191060 A1 | 7/2012 | Banister et al. | |
| 2012/0209627 A1 | 8/2012 | Moncrief et al. | |
| 2013/0008436 A1* | 1/2013 | Von Hollen | A61M 15/0086 128/200.14 |
| 2013/0041680 A1 | 2/2013 | Klien | |

(Continued)

FOREIGN PATENT DOCUMENTS

WO WO-2013043607 A1 * 3/2013 ........... A61F 9/0008

OTHER PUBLICATIONS

Miller et al., The Anatomy of decision support during inpatient care provider order entry (CPOE): Empirical observations from a decade of CPOE Experience at Valderbilt, Journal of Biomedical Informatics, 38, 469-485 (2005).

(Continued)

*Primary Examiner* — Joy Chng
(74) *Attorney, Agent, or Firm* — Perkins Coie LLP

(57) ABSTRACT

A therapeutic event such as administering a medication is established. A trigger is established for the therapeutic event, the trigger being a status of some condition. A determination is made as to whether the trigger is present. A prompt is established for the therapeutic event. If the trigger is present, the prompt is delivered to a subject such as a patient. A determination is able to be made as to whether the prompt is delivered, and/or whether the therapeutic event is executed by the subject.

59 Claims, 14 Drawing Sheets

(56) References Cited

U.S. PATENT DOCUMENTS

2013/0276785 A1 10/2013 Melker et al.
2014/0077946 A1* 3/2014 Tran .................... G06F 19/3418
340/539.13

OTHER PUBLICATIONS

International Search Report and Written Opinion for International Patent Application No. PCT/US2014/063505 dated Apr. 1, 2015, 13 pages.

* cited by examiner

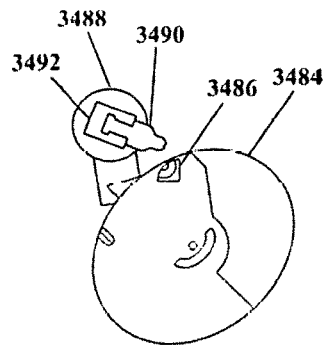
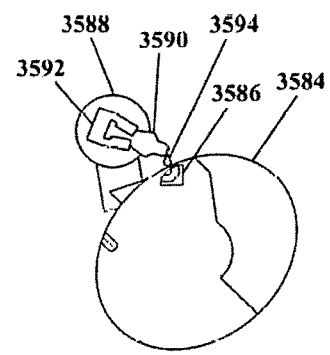
FIG. 34            FIG. 35
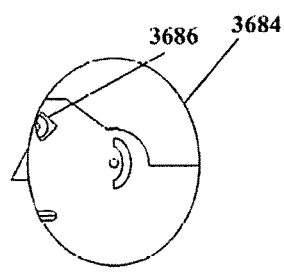
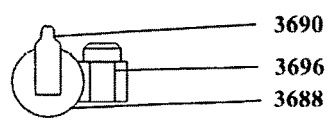
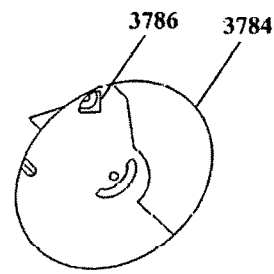
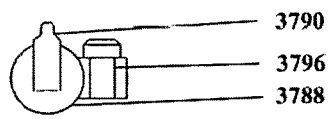
FIG. 36            FIG. 37

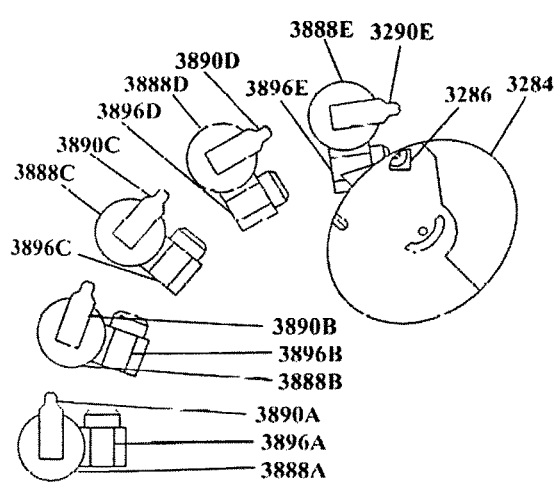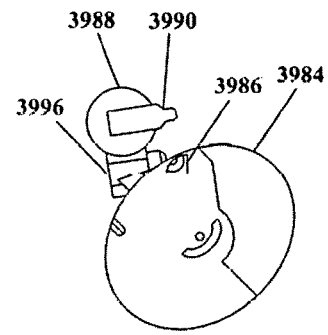
FIG. 38  FIG. 39
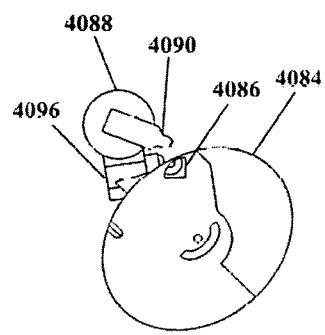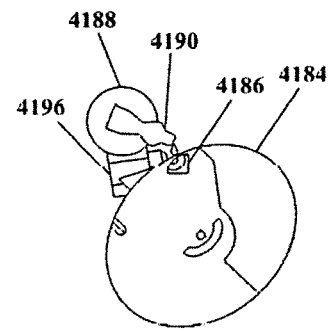
FIG. 40  FIG. 41

METHOD OF AND APPARATUS FOR TARGETED INTERACTIVE HEALTH STATUS NOTIFICATION AND CONFIRMATION

CLAIM TO PRIORITY

This application claims the benefit of U.S. Provisional Application Ser. No. 61/898,439 filed on Oct. 31, 2013, the contents of which are incorporated by reference for all purposes.

FIELD OF THE INVENTION

This invention relates to the targeted, interactive delivery of information and instructions, and the collection of responses thereto. More particularly, the invention relates to approaches for sending information and instructions regarding health-related matters targeted to and/or tailored for recipients thereof, to determining what responses might be made by the recipients, and to collecting data therefrom. The invention includes, but is not limited to, applications regarding health and health status of the recipients.

DESCRIPTION OF RELATED ART

Information regarding many topics, for example health care, is proliferating. Access to information when making decisions, carrying out activities, etc. is valuable, but excessive, irrelevant, or inadequately-targeted information can itself be problematic, since remembering and associating the information appropriately to the current situation becomes increasingly difficult as the amount of available information increases. This is particularly true when individuals must consider information in a complex field, without having comprehensive training in that field. An example of this would be medical patients, who is in a position to control their own health-related circumstances, but who also typically lack extensive medical training.

Spoken instructions, e.g. from a doctor during a health care visit, can provide some level of guidance. Likewise, printed instructions such as those accompanying a prescription for medication also can provide guidance. However, such instructions are limited in scope, for example being essentially static. That is, a written prescription or visit can inform a patient of the need to take a medication at a particular time or under a particular circumstance, but does not provide a reminder at that time or under that circumstance. Even an automated reminder system, such as a timed alarm, provides only limited information, and is often readily ignored, overlooked, etc. Moreover, alarms typically do not in themselves either confirm compliance (i.e. did the patient take his or her medication), nor collect data, nor offer an opportunity for feedback from the patient. While such arrangements might be implemented by live persons, e.g. real-time personal reminders from physicians or other trained persons, such approaches are for many cases logistically impractical.

BRIEF SUMMARY OF THE INVENTION

The present invention contemplates a variety of systems, apparatus, methods, and paradigms for targeted and/or interactive approaches for delivering health-related information and instructions, and/or for receiving confirmation of receipt, compliance, etc.

In one embodiment of the present invention, a machine-implemented method is provided, the method including in a processor establishing at least one therapeutic event, establishing at least one trigger for the therapeutic event, the trigger including a status of a condition, determining whether the trigger is present, establishing a prompt for the therapeutic event, and/or if the trigger is present delivering the prompt to at least a first subject.

The therapeutic event includes administering a medication, utilizing a medical device, acquiring a subject status, performing an exercise, taking a break from an activity, and/or exiting an area.

The condition includes a time, a subject identity, a subject action, a subject status, and/or an environmental feature.

The condition includes a subject status, and/or the subject status includes bioinformation regarding the subject.

Determining whether the trigger is present including sensing the condition, determining a time, sensing a status of the subject, sensing bioinformation regarding the subject, and/or sensing the condition using a portable electronic device.

The prompt includes an auditory signal, a visual signal, a tactile signal, a verbal message, a tone, a musical sequence, a text message, a vibration, a telltale light, a visual image, an animation, a change in audio output, and/or a change in video output.

The method includes delivering the prompt so as to evoke at least a portion of a medical effect associated with an absence of the therapeutic event.

The prompt includes obscuring at least a portion of a display visible to the subject.

The method includes progressively obscuring the display, such that the portion thereof increases over time.

The prompt includes obscuring at least a portion of a display visible to the subject, the obscuring initiating in a periphery of the display, the obscuring progressing over time so as to increase the portion, the obscuring progressing such that the portion expands substantially toward a center of the display.

The prompt includes obscuring at least a portion of a display visible to the subject, the obscuring initiating proximate a center of the display, the obscuring progressing over time so as to increase the portion, the obscuring progressing such that the portion expands substantially away from a center of the display.

The prompt includes obscuring at least a portion of a display visible to the subject with at least one icon, the icon includes a representation of a microorganism, a number of the at least one icon increasing over time so as to increase the portion.

The prompt is able to be contextually relevant.

The method includes delivering the prompt via a portable electronic device, a wearable electronic device, a smart phone, a personal data assistant, a tablet, a smart watch, a head mounted display, a laptop computer, and/or a desktop computer.

The method includes delivering the prompt can include altering an output of a visual display.

The method includes delivering the prompt can include altering the output of the visual display in a manner substantially corresponding with an effect associated with not executing the therapeutic event.

The prompt includes an advisory, the prompt can include at least one of a health advisory, information regarding an environmental factor, and/or an instruction.

The prompt includes at least one of instruction to administer a medication, an instruction to utilize a medical device, an instruction to acquire a subject status, an instruction to perform an exercise, an instruction to take a break from an activity, and/or an instruction to exit an area.

The first subject includes a caregiver for a patient, a portable electronic device, a smart phone, a personal data assistant, a tablet, a smart watch, a head mounted display, a laptop computer, a desktop computer, a health professional, emergency services, and/or a data store.

The method includes determining whether the therapeutic event is executed.

The method includes determining whether the therapeutic event is executed can include action recognition, receiving data from at least one sensor, and/or sensing a manipulation of a medication dispenser.

The method includes determining whether the therapeutic event is executed can include receiving data from an image, an accelerometer, a gyroscope, and/or a pressure sensor.

The method includes determining whether the therapeutic event is executed can include sensing a manipulation of a medication dispenser.

Sensing the manipulation of the medication dispenser includes receiving data from at least one sensor proximate the medication dispenser, receiving data from at least one sensor distal to the medication dispenser, visually sensing at least a portion of the medication dispenser, and/or visually sensing a target on the medication dispenser.

Sensing the manipulation of the medication dispenser includes visually sensing a target on the medication dispenser, the target can include a bar code, a QR code, a static LED, a color-modulated LED, and/or an intensity-modulated LED.

Determining whether the therapeutic event is executed can include sensing a subject action.

The subject action can be characteristic of the therapeutic event.

The therapeutic event can include administering a medication.

The subject action can include administering an eye drop.

The subject action includes the subject tilting back his/her head thereof, the subject raising a hand thereof from a first position substantially in front of the subject to a second position substantially above his/her head, the subject inclining the hand substantially in a direction of his/her eye, and the subject squeezing the hand.

The method includes sensing the subject action with at least one sensor, and the sensor can include a sensor held in a hand of the subject, a sensor engaged with a wrist of the subject, and/or a sensor engaged with a medication container, the medication container being held in a hand of the subject.

The sensor includes an accelerometer, a gyroscope, and/or a pressure sensor.

The medication container includes an eyedrop bottle.

The sensor includes a microphone disposed within the medication container.

The medication container includes an inhaler.

The method includes establishing at least one confirmation of the therapeutic event, and if the therapeutic action is executed, executing the confirmation of the therapeutic event.

The confirmation includes an auditory signal, a visual signal, a tactile signal, a verbal message, a tone, a musical sequence, a text message, a vibration, a telltale light, a visual image, an animation, a change in audio output, a change in video output, and/or generating a data entry.

The confirmation includes a time of the therapeutic event.

The confirmation includes recording a data entry on a data store disposed in a medication dispenser, a medical device, a PDA, a smart phone, a smart watch, a head mounted display, a tablet, a laptop computer, and/or a desktop computer.

The method includes delivering the confirmation to the first subject and/or a second subject.

The method includes delivering the confirmation to a caregiver, a portable electronic device, a smart phone, a personal data assistant, a tablet, a smart watch, a head mounted display, a laptop computer, a desktop computer, a health professional, emergency services, and/or a data store.

In another embodiment of the present invention, a machine implemented method is provided, the method including in a processor establishing at least one therapeutic event, and establishing at least one trigger for the therapeutic action, the trigger including a status of a condition. The method includes determining whether the trigger is present, establishing a prompt for the therapeutic event, and if the trigger is present, delivering the prompt to at least a first subject. The method further includes determining whether the therapeutic event is executed, and if the therapeutic action is executed, establishing at least one confirmation of the therapeutic event.

The method includes delivering the prompt so as to evoke at least a portion of a medical effect associated with an absence of the therapeutic event.

In another embodiment of the present invention, a machine implemented method is provided, the method including in a processor establishing at least one therapeutic event, and establishing at least one trigger for the therapeutic action, the trigger including a status of a condition. The method includes determining whether the trigger is present, establishing a prompt for the therapeutic event, and if the trigger is present delivering the prompt to a first subject and delivering the prompt to a second subject.

In some embodiments, the method includes delivering a financial transaction from the second subject to the first subject.

In some embodiments, the ownership of the status of the condition remains unchanged.

In an aspect, an apparatus includes a processor adapted to determine a presence of a trigger for a therapeutic event, wherein the trigger includes a status of a condition, and a prompter adapted to deliver a prompt to a subject if the processor determines the presence of the trigger.

In some embodiments, the processor is disposed in a medication container, a wrist device, a smart phone, a smart watch, a tablet, a PC, a television, and/or a set-top box.

In some embodiments, the prompter includes a display screen, an LED, an audio speaker, and/or a haptic output.

In some embodiments, the prompter is disposed in a medication container, a wrist device, a smart phone, a smart watch, a tablet, a PC, a television, and/or a set-top box.

In some embodiments, at least one sensor is in communication with the processor, wherein the sensor is adapted to determine the status of the condition.

In some embodiments, the sensor is disposed on a medication container, a wrist device, a smart phone, a smart watch, a tablet, a PC, a television, and/or a set-top box.

In some embodiments, the sensor includes an imager, a depth mapper, an accelerometer, a gyroscope, a pressure sensor, a code reader, and/or a microphone.

In some embodiments, the apparatus includes an inputter, wherein the inputter is adapted to receive a confirmation that the prompt is received and/or a confirmation that the therapeutic event is executed.

In some embodiments, the processor is adapted to establish a confirmation of a receipt of the prompt and/or an execution of the therapeutic event.

In some embodiments, the apparatus includes a sensor in communication with the processor, the sensor being adapted to sense the confirmation.

In some embodiments, the sensor is disposed on a medication container, a wrist device, a smart phone, a smart watch, a tablet, a PC, a television, and/or a set-top box.

In some embodiments, the sensor includes an imager, a depth mapper, an accelerometer, a gyroscope, a pressure sensor, a code reader, and/or a microphone.

In some embodiments, the apparatus includes a therapeutic event entity instantiated on the processor, the therapeutic event entity being adapted to establish information regarding a therapeutic event, a trigger entity instantiated on the processor, the trigger entity being adapted to establish a trigger for the therapeutic event, the trigger including a status of a condition, a prompt entity instantiated on the processor, the prompt entity being adapted to establish a prompt for the therapeutic event, a trigger determiner entity instantiated on the processor, the trigger determiner entity being adapted to determine whether the trigger is present, a prompter entity instantiated on the processor, the prompter entity being adapted to deliver the prompt to a subject.

In some embodiments, the apparatus includes a confirmation determiner entity instantiated on the processor, the confirmation determiner entity being adapted to determine a delivery of the prompt and/or an execution of the therapeutic event.

In some embodiments, the apparatus includes a confirmer entity instantiated on the processor, the confirmer entity being adapted deliver a confirmation that a delivery of the prompt and/or an execution of the therapeutic event.

In another aspect, an apparatus, includes means for establishing at least one therapeutic event, means for establishing at least one trigger for the therapeutic event, the trigger including a status of a condition, means for determining whether the trigger is present, means for establishing a prompt for the therapeutic event, and means for, if the trigger is present, delivering the prompt to at least a first subject.

In another aspect, an apparatus includes means for establishing at least one therapeutic event, means for establishing at least one trigger for the therapeutic event, the trigger including a status of a condition, means for determining whether the trigger is present, means for establishing a prompt for the therapeutic event, means for, if the trigger is present, delivering the prompt to at least a first subject, means for establishing at least one confirmation of the therapeutic event, and means for, if the therapeutic action is executed, executing the confirmation of the therapeutic event.

A method, includes instantiating on a processor executable instructions adapted to establish at least one therapeutic event, instantiating on a processor executable instructions adapted to establish at least one trigger for the therapeutic event, the trigger including a status of a condition instantiating on a processor executable instructions adapted to determine whether the trigger is present, instantiating on a processor executable instructions adapted to establish a prompt for the therapeutic event, and instantiating on the processor executable instructions adapted to deliver the prompt to at least a first subject if the trigger is present.

In some embodiments, the method includes instantiating on the processor executable instructions adapted to establish at least one confirmation of the therapeutic event.

In some embodiments, the method includes instantiating on the processor executable instructions adapted to execute the confirmation of the therapeutic event if the therapeutic action is executed.

In another aspect, a machine-implemented method includes a first subject collecting health data regarding a second subject, upon receipt by the first subject of a prompt thereto, the first subject sending the health data to a third subject.

In some embodiments, the first subject includes an electronic device and/or a wearable device.

In some embodiments, the second subject includes a patient.

In some embodiments, the third subject includes a database.

In some embodiments, the health data includes an identity of the second subject.

In another aspect, a method includes instantiating in a processor in a first subject executable instructions adapted to collect health data regarding a second subject, instantiating in the processor executable instructions adapted to send the health data to a third subject upon receipt by the first subject of a prompt thereto.

In some embodiments, the first subject includes an electronic device and/or a wearable device.

In some embodiments, the second subject includes a patient.

In some embodiments, the third subject includes a database.

In some embodiments, the health data includes an identity of the second subject.

In another aspect, a machine-implemented method, includes in a substantially uncontrolled environment, with a first subject, acquiring a plurality of statuses of at least one condition, the condition being relevant to a health of a second subject, conveying the statuses of the at least one condition to a third subject.

In some embodiments, the environment includes a substantially unrestricted space.

In some embodiments, the environment substantially lacks live medical supervision of the second subject.

In some embodiments, the first subject includes at least one of a portable electronic device and/or a wearable device.

In some embodiments, the first subject includes a smart phone, a personal data assistant, a tablet, a wearable health sensor, a smart watch, and/or a head mounted display.

In some embodiments, the method includes sensing the statuses with a sensor disposed on the first subject.

In some embodiments, the sensor includes an imager, an accelerometer, a microphone, and/or a gyroscope.

In some embodiments, the condition includes an action executed by the second subject, an action executed on the second subject, an event proximate the second subject, an environmental feature proximate the second subject, and/or bio-information regarding the second subject.

In some embodiments, the condition includes the action executed by the second subject, the action can include administering a medication, utilizing a medical device, executing a therapy, and/or performing an activity.

In some embodiments, the activity include sleeping, lying down, sitting, standing, walking, jogging, running, consuming food, and/or consuming drink.

In some embodiments, the condition includes the action executed on the second subject, the action include administering a medication, utilizing a medical device, and/or executing a therapy.

In some embodiments, the condition includes the environmental feature proximate the second subject, the environment feature may include time, temperature, humidity, air pressure, presence of pollutants, concentration of pollutants, presence of allergens, concentration of allergens, presence of toxins, concentration of toxins, level of visible light, rate of change of visible light, and/or level of ultraviolet light.

In some embodiments, the condition includes bio-information regarding the second subject, the bio-information may include medication concentration, heartbeat, respiration, body temperature, brain waves, blood oxygen, blood chemistry, and/or body position.

In some embodiments, the third subject includes a database.

In some embodiments, the method includes conveying the statuses in response to a prompt to the first and/or second subjects.

In another aspect, a method includes instantiating in a processor in a first subject executable instructions adapted to acquire with the first subject a plurality of statuses of at least one condition, the condition being relevant to a health of a second subject, instantiating in the processor executable instructions adapted to convey the statuses of the at least one condition to a third subject.

In some embodiments, the first subject includes a portable electronic device, a wearable device, a smart phone, a personal data assistant, a tablet, a wearable health sensor, a smart watch, and/or a head mounted display.

In one embodiment, the method includes sensing bio-information regarding the subject. Determining whether the trigger is present can include sensing the condition using a portable electronic device.

The prompt is able to be an auditory signal, a visual signal, and/or a tactile signal. The prompt can include a verbal message, a tone, a musical sequence, a text message, a vibration, a telltale light, a visual image, an animation, a change in audio output, and/or a change in video output.

The method can include delivering the prompt so as to evoke at least a portion of a medical effect associated with an absence of the therapeutic event.

The prompt can include obscuring at least a portion of a display visible to the subject.

BRIEF DESCRIPTION OF THE SEVERAL VIEWS OF THE DRAWINGS

Like reference numbers generally indicate corresponding elements in the figures.

FIG. 30 through FIG. 35 show an example embodiment of automatic confirmation and/or sensing execution of a therapeutic event, according to the present invention.

FIG. 36 through FIG. 41 show another example embodiment of automatic confirmation and/or sensing execution of a therapeutic event, according to the present invention.

DETAILED DESCRIPTION OF THE INVENTION

Figure 1:
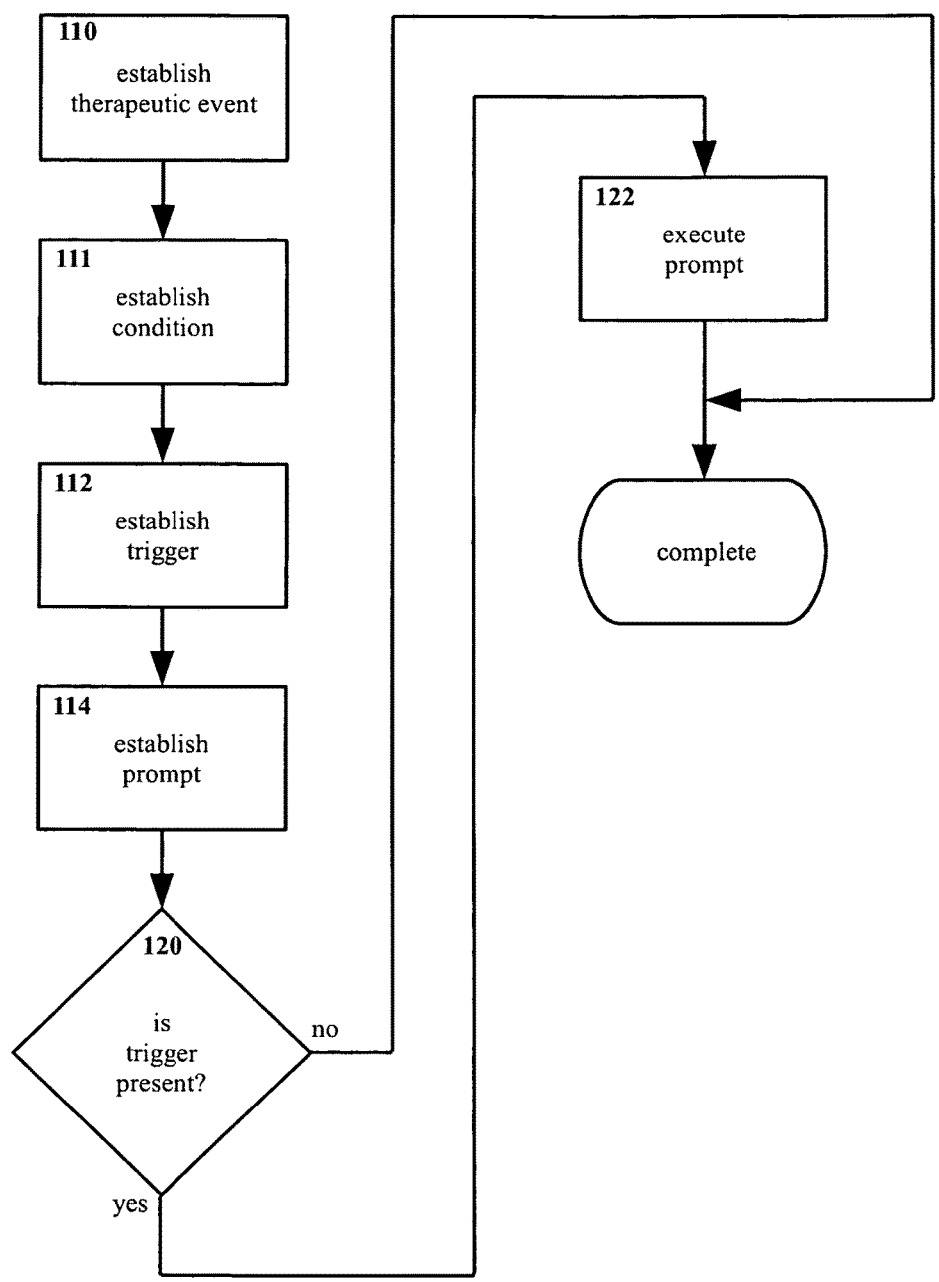
FIG. 1 shows an example embodiment of a method for targeted interactive notification according to the present invention.

With reference to FIG. 1, therein is shown an example embodiment of a method for targeted interactive notification according to the present invention.

In the example method of FIG. 1, a therapeutic event is established 110. A therapeutic event is able to be substantially any event or action relating in some fashion to health, health maintenance, safety, etc. Typically, though not necessarily, a therapeutic event relates to a particular individual subject (e.g. a patient receiving health care). Also typically, though again not necessarily, a therapeutic event is action that is necessary or desirable for health. For example, therapeutic events includes, but are not limited to, administering a medication, avoiding sunlight or pollen (e.g. for persons sensitive thereto), contacting a health professional, sensing some form of bio-information such as pulse rate or blood pressure, providing feedback, recording and/or transmitting data, and measuring an environmental parameter such as temperature or air pressure.

A therapeutic event is able to be negative. That is, not operating machinery for some period of time after taking a medication could constitute a therapeutic event.

The present invention is not particularly limited with regard to what constitutes a therapeutic event, and events other than those described are able to be equally suitable. More discussion of potential therapeutic events is presented later herein.

A condition is established 111. A condition is some feature, parameter, etc. that is able to be relevant to a health matter and/or a specific therapeutic event. A condition is able to be time, temperature, location, blood pressure, etc. A condition is able to be related to a trigger, described below.

The present invention is not particularly limited with regard to what constitutes a condition, and condition other than those described may be equally suitable. More discussion of potential conditions is presented later herein.

Moving on in FIG. 1, a trigger is established 112. A trigger is an event, value, etc. for the condition under which the therapeutic event is desirable and/or necessary. It will be understood that actions that are beneficial in certain situations may be harmful in other situations, and vice versa. The trigger thus specifies the situations under which a particular therapeutic event is desirable.

Typically, though not necessarily, triggers may consider conditions and/or other factors such as a time of day, a location, a level of some ambient condition(s), bio-information regarding the subject or another person, actions of the subject or another person, etc. Triggers also include inputs from recognized sources, e.g. an instruction from a health care provider might constitute a trigger.

A trigger is able to be negative. That is, a trigger is able to include the absence of certain parameters. For example, a trigger can only indicate desirability to take a medication if the subject is not currently operating a motor vehicle, or if the subject is alone with no one else present to accompany/observe them, etc.

The present invention is not particularly limited with regard to what constitutes a trigger, and triggers other than those described may be equally suitable. More discussion of potential triggers is presented later herein.

Therapeutic events, conditions, and triggers typically are linked, in that each therapeutic event typically is governed by a trigger which is an event or level of some condition, and each trigger typically governs a therapeutic event. However, a one-to-one correspondence is not required (though one-to-one correspondence also is not prohibited). That is, a therapeutic event is able to be governed by more than one trigger, and/or a trigger may govern more than one therapeutic event. Likewise, a trigger is able to be considered more than one condition, and a single condition may affect more than one trigger.

Continuing in FIG. 1, a prompt is established 114. The prompt is an invocation of the therapeutic event. That is, if a therapeutic is for a subject to administer a medication, an associated prompt might be a text message sent to the subject reminding the subject to administer the medication. Likewise, if a therapeutic event is to measure the pulse rate of a subject through some sensor, an associated prompt might be an instruction to that sensor to execute the measurement.

Typically, a prompt will include delivery of health-related information, instructions, and/or inquiries. For example, information includes a subject's current blood pressure, the airborne pollen count at a particular time and place, a caution that low air pressure might trigger an asthma attack, etc. Health instructions include a directive to administer a medication, to engage in or avoid some activity for a period of time (e.g. not to sleep or lie down within an hour after taking glaucoma medication), to seek out shade (e.g. to avoid overheating), etc. Health inquiries might include requesting comments from a subject regarding side effects experienced after medication has been taken, asking that a health professional be contacted, acquiring data through a sensor (e.g. measuring ambient temperature), etc.

Prompts is able to be delivered to persons, devices, and/or entities other than the direct subject of the prompt. That is, an instruction to administer a medication to a first subject might be delivered to a second subject, e.g. a parent who must administer the medication to a child. As another example, a prompt for a sensor to measure a subject's blood pressure might be sent to the sensor itself, e.g. if the sensor is already in a position to take the measurement (such as a sensor on a smart phone, wearable device, etc.).

The present invention is not particularly limited with regard to what may constitute a prompt, and prompts other than those described may be equally suitable. More discussion of potential prompts is presented later herein.

Prompts are linked with therapeutic events, conditions, and triggers, in that prompts are invoked by triggers in support of some useful or necessary therapeutic event. However, as noted previously with regard to therapeutic events, conditions, and triggers, a one-to-one correspondence therebetween (though one-to-one correspondence also is not prohibited).

As a brief illustrative summation, a therapeutic event is a desired action or event, a condition is a feature that is to be considered in determining whether the event or action is desirable, a trigger is the value of the condition under which the event or action is desirable, and the prompt is a message sent or action delivered to invoke the response.

In establishing a therapeutic event 110, establishing a condition 111, establishing a trigger 112, and/or establishing a prompt 114, typically although not necessarily the therapeutic event, condition, trigger, and/or prompt may be pre-defined, for example as data and/or executable instructions within a processor. However, the present invention is not particularly limited with regard to how a therapeutic event, condition, trigger, and/or prompt may be established, and other approaches, including but not limited to communication of a therapeutic event from an external source or determination e.g. by a processor following executable instructions, maybe equally suitable.

Continuing in FIG. 1, a determination is made 120 as to whether a trigger (as established in step 112) is present, and/or is satisfied. For example, if the trigger under consideration is "at 7:00 PM" (with the condition presumably being "time" for such an instance), the determination 120 might constitute a determination as to whether the current time is 7:00 PM.

It will be understood that the particulars of the determination 120 for any particular embodiment will depend at least in part on the nature of the condition and trigger associated therewith. However, the present invention is not particularly limited insofar as how the determination 120 of whether the trigger is present may be carried out. Typically although not necessarily the determination 120 may be made using executable instructions and/or within a processor. For such embodiments, data used for the determination 120 is able to for example be internal (e.g. time data from an internal chronometer), stored (e.g. data read from a hard drive or other data store), external (e.g. data sent from a network), experimental (e.g. data obtained from a sensor controlled by the processor), etc.

If the determination 120 regarding the presence of the trigger is positive—that is, if the trigger is present and/or satisfied (or stated differently the status of the condition is such that the therapeutic event is to be executed)—the method continues with execution of the prompt 122. For example, the instructions are sent, the sensor reading is taken, etc. as determined by the prompt (established in step 114).

If the determination 120 regarding the presence of the trigger is negative—if the trigger is not present and/or satisfied (or, the status of the condition is such that the therapeutic event is not to be executed)—the method is shown in FIG. 1 is complete.

However, although FIG. 1 shows the method therein as being complete following step 122, it is emphasized that the method in FIG. 1 is an example only. Other steps, other functions, etc. can be incorporated into the method, and/or other methods may be executed in combination with the method according to the present invention. In addition, for at least certain embodiments the method may repeat, e.g. in an ongoing loop back to step 120 so as to determine on an ongoing basis whether the trigger is present.

Figure 2:
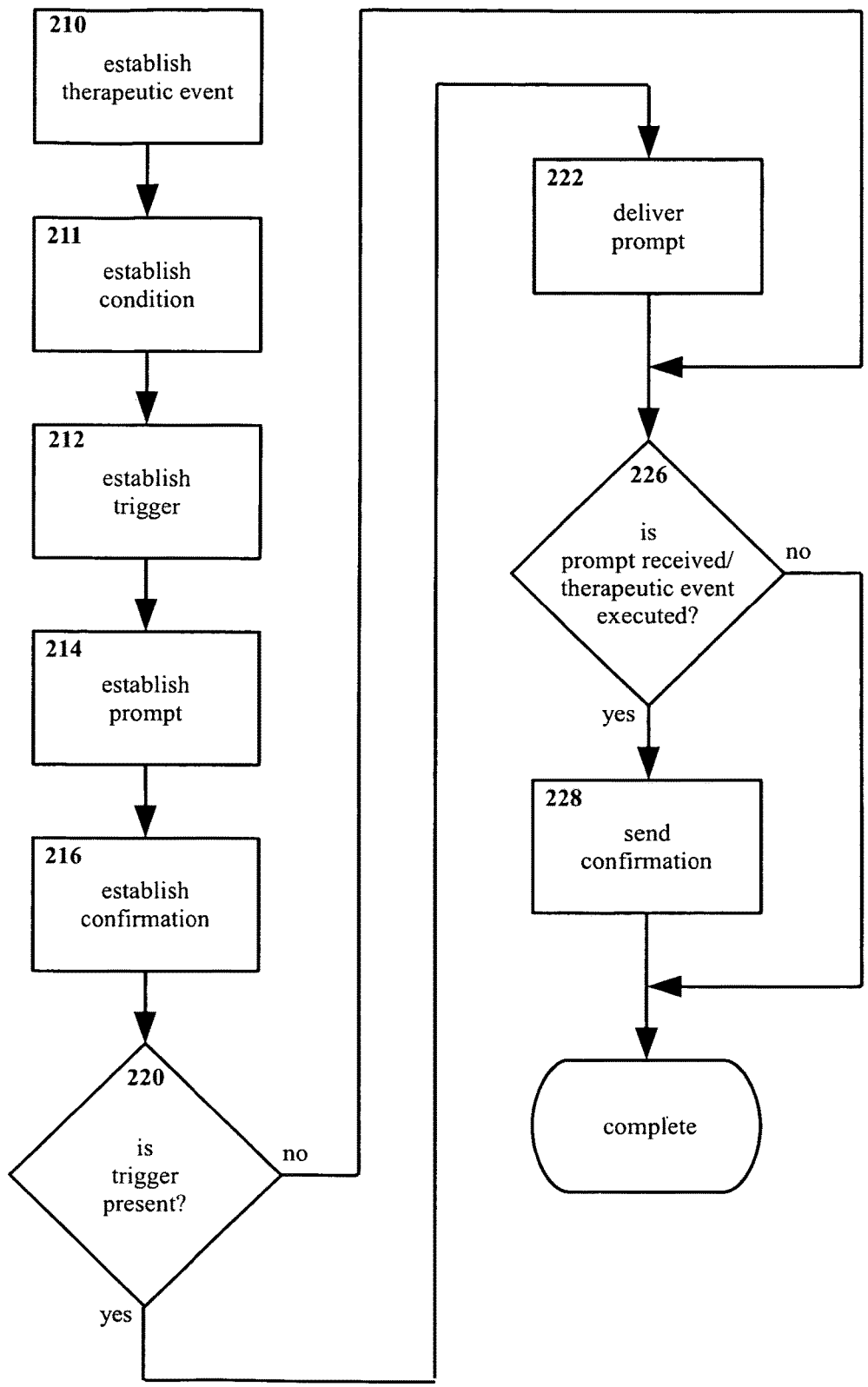
FIG. 2 shows an example embodiment of a method for targeted interactive notification with confirmation according to the present invention.

Moving on to FIG. 2, therein is shown an example embodiment of a method for targeted interactive notification according to the present invention, with confirmation incorporated therein.

In the method according to FIG. 2, a therapeutic event is established 210, a condition is established 211, a trigger is established 212, and a prompt is established 214. Therapeutic events, conditions, triggers, and prompts have been described previously herein.

The method also includes establishing a confirmation 216. A confirmation is a response to a prompt, typically though not necessarily indicating that the prompt has been received and/or that the therapeutic event for which the prompt was delivered has been executed.

For example, a confirmation to a prompt to administer a medication might include a text message indicating receipt of the prompt, data from a sensor that verifies that the medication has been administered, an image of the medication container and/or the medication being administered, a message logging the time at which the medication was administered, etc.

The present invention is not particularly limited with regard to what may constitute a confirmation, and confirmations other than those described may be equally suitable. More discussion of potential confirmations is presented later herein.

Confirmations may require deliberate action, e.g. on the part of the subject of the therapeutic event, and/or may function in a semi-automatic or fully-automatic fashion. It is noted that confirmations are not necessarily limited to being sent by the subject of the therapeutic event, or even by the recipient of the prompt. For example, as noted above a prompt to administer medication to a first subject such as a child might be sent to a second subject such as a parent; a prompt might similarly be sent by the second subject (the parent) rather than the first subject (the child to whom the medication is administered). Likewise, confirmations are not necessarily limited to being sent to the entity that established that delivers the prompt. For example, a therapeutic event might be generated by a computer screen being used by a subject, with the confirmation being delivered by smart phone. As another example, a computer at a medical center might send a prompt, while the confirmation is sent to a different computer, a database, etc.

Moving on in FIG. 2, a determination is made 220 as to whether the trigger is present/satisfied. If the trigger is present and/or satisfied, the method continues with delivering the prompt 222, then continuing on to step 226 (below). If the trigger is not present and/or satisfied, the method proceeds with step 226 (below).

In step 226, a determination is made as to whether the prompt is received, and/or as to whether the therapeutic event has been executed. For example, if the prompt is an instruction to administer medication, the confirmation might be that the instruction was received, or that the medication was administered, etc. The particulars of how the determination 226 is to be made will depend at least in part on the nature of the confirmation, and/or possibly on the nature of the prompt. Typically, though not necessarily, an automated system may determine whether a prompt has been received, and/or whether the therapeutic event associated therewith has been executed.

If the determination 226 is positive—if the prompt is received and/or the therapeutic event is executed—then the method proceeds with sending the confirmation 228. If the determination 226 is negative—if the prompt is not received, and/or the therapeutic event is not executed—then the method is complete.

In the arrangement shown in FIG. 2, it is assumed that either a confirmation that a prompt was received will be sent 228, or a confirmation that the therapeutic event was executed will be sent 228. However, the present invention is not limited only to such alternatives. For example, for certain embodiments a first confirmation might be sent 228 regarding receipt of the prompt, with a second confirmation being sent 228 regarding execution of the therapeutic event. Other arrangements also may be equally suitable.

With reference now to both FIG. 1 and FIG. 2, in broad terms the example methods therein include determining whether some health-related action (the therapeutic event) is called for (the trigger is present), in which case a person or other target (the subject) is advised/instructed/queried regarding the health-related action. For the example of FIG. 2, some response (the confirmation) is also sent, possibly though not necessarily by the subject to the source of the prompt. However, it is emphasized that these are examples only, and other arrangements may be equally suitable.

Figure 3:
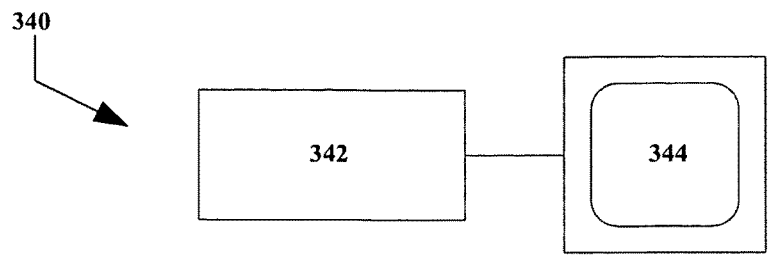
FIG. 3. shows an example embodiment of an apparatus for targeted interactive notification according to the present invention.

Now with reference to FIG. 3, a hardware schematic for an example embodiment of an apparatus 340 according to the present invention is shown therein.

The example apparatus 340 includes a processor 342. The processor 342 is adapted to determine the presence of a trigger for a therapeutic event, e.g. a trigger being some value of or event in some condition. Typically, though not necessarily, the processor 342 may store and/or generate information regarding therapeutic events, conditions, and/or triggers, and/or may determine the presence of the trigger using executable instructions instantiated on the processor 342.

The invention is not particularly limited with regard to the choice of processor 342. Suitable data processors 342 include but are not limited to digital electronic microprocessors. Although the processor 342 is referred to in at least some places herein as a self-contained physical device for purposes of clarity, this is not required, and other arrangements is able to be suitable. For example, the processor 342 constitutes two or more physical processors working cooperatively, a processing capability in a network without a well-defined physical form, etc. Likewise, although data is able to be referred to herein as being stored on the processor 342, this language should be understood to include the use of data stores that physically may be physically distinct from the processor 342, such as a hard drive or flash drive in communication with the processor 342, cloud storage, etc.

The apparatus 340 also includes a prompter 344 in communication with the processor 340. The prompter 344 is adapted to deliver a prompt to a subject if the processor determines the presence of the trigger.

The present invention is not particularly limited with regard to the type of prompter 344. The particulars of a prompter is able to at least some degree depend on the nature of the prompt to be delivered (and/or vice versa). The prompter 344 can for example be a visual display adapted to deliver images, text, animations, etc. Other prompters 344 may include, but are not limited to, audio speakers adapted to deliver speech, tones, music, etc., LEDs or other indicators adapted to serve as tell-tales, haptic or tactile systems adapted to vibrate or otherwise generate physical sensations, data systems adapted to send data signals to automated devices such as sensors, etc. These are examples only, and other arrangements may be equally suitable.

Although in FIG. 3 the processor 342 and prompter 344 are shown to be in direct communication, i.e. using wires, this is an example only. The present invention is not particularly limited with regard to how communication is executed or what mechanisms are used therefor, and wireless communication and/or other arrangements may be equally suitable.

Figure 4:
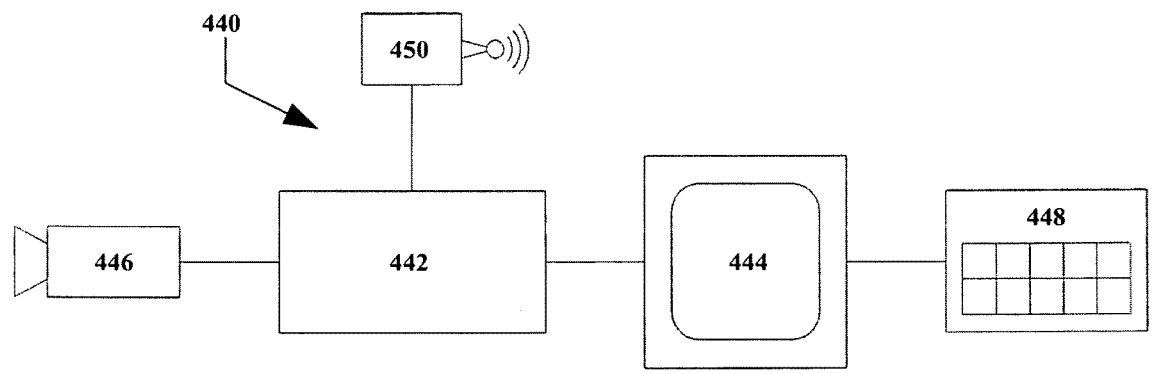
FIG. 4 shows another example embodiment of an apparatus for targeted interactive notification according to the present invention.

Now with reference to FIG. 4, a hardware schematic for another example embodiment of an apparatus 440 according to the present invention is shown therein. The example embodiment of an apparatus 440 according to the present invention as shown therein includes a processor 442 and a prompter 444. In addition, as shown in FIG. 4 the apparatus may include additional elements.

For example, the apparatus 440 can include a sensor 446. The sensor 446 is able to be adapted to deliver a confirmation that a prompt was delivered, and/or to deliver a confirmation that a therapeutic event was executed. For example, considering administration of a medication as a therapeutic event, a sensor 446 in the form of an imager might capture an image indicating that a medication has been administered, a code scanner might detect a bar code, QR code, etc. on a container of medication so as to determine that the container was at some position within the scanner's field of view (and thus allowing it to be inferred that the medication was administered), a pressure or motion sensor on the medication container might detect characteristic motions of or pressures applied to the container that would correspond with administration of the medication, etc.

Additionally or alternatively, the sensor 446 may be adapted to sense a trigger for a therapeutic event. Again considering administration of a medication as the relevant therapeutic event, a sensor 446 might detect a level of blood sugar in a subject with diabetes so as to support determination of whether that subject is in need of an insulin injection.

These are examples only, and other sensors 446 and tasks therefore is able to be equally suitable. Although the sensor 446 as shown in FIG. 4 is depicted as a camera, the present invention is not limited only thereto.

The apparatus 440 is able to include an inputter 448. The inputter 448 is able to be adapted to accept and/or deliver input from a subject (including but not limited to a person), for example to provide a confirmation that a prompt was delivered, and/or to deliver a confirmation that a therapeutic event was executed. For example, a keypad or audio sensor might accept text input or voice responses, etc. An inputter 448 is able to also accept responses if the therapeutic event is or includes a request for information, for example if the therapeutic event is a solicitation for patient impressions and/or reports of side effects at various times following administration of a medication the inputter 448 is able to accept such information and deliver the information to some destination (e.g. the processor 442, some external system, etc.).

Again, these are examples only, and other inputters 448 and tasks therefor is able to be equally suitable. Although the inputter 448 as shown in FIG. 4 is depicted as a keypad, the present invention is not limited only thereto.

It is noted that certain aspects of the functionality of the sensor 446 and the inputter 448 is able to, either individually or collectively, be considered to be similar. That is, either or both the sensor 446 and the inputter 448 is able to be adapted to provide confirmation of receipt of a prompt and/or to provide confirmation of execution of a therapeutic event. Thus, for at least certain embodiments, the sensor 446 and the inputter 448 is able to be considered and/or referred to, individually or collectively, to serve as a confirmer. An embodiment of an apparatus 440 thus is able to be considered to include a confirmer even if the apparatus 440 includes only one of a sensor 446 and an inputter 448, and/or for an embodiment of an apparatus 440 having both a sensor 446 and an inputter 448 the sensor 446 and inputter 448 collectively may be considered a confirmer for that apparatus 440. Nevertheless it is noted that an apparatus 440 may include a sensor and/or an inputter that does not function as a confirmer, while still being within the scope of the present invention.

Still with regard to FIG. 4, the apparatus 440 may include a communicator 450. The inputter 450 may be adapted to communicate with other devices, systems, networks, etc. that are not already in communication with the processor 442, prompter 444, sensor 446, and/or inputter 448. For example, if the apparatus 440 shown in FIG. 4 is considered as a single physical unit, such as a smart phone, the communicator 450 may be adapted to provide one-way or two-way wireless communication with other systems, such as a computer at a health care facility, a cell phone of a friend, caretaker, or health professional, etc.

These are examples for a communicator 450 only, and the present invention is not limited only thereto.

As noted above, certain embodiments of an apparatus according to the present invention, such as the example embodiment shown in FIG. 4, may (though are not required to be) single physical units such as cell phones. However, other arrangements may be equally suitable.

Figure 5:
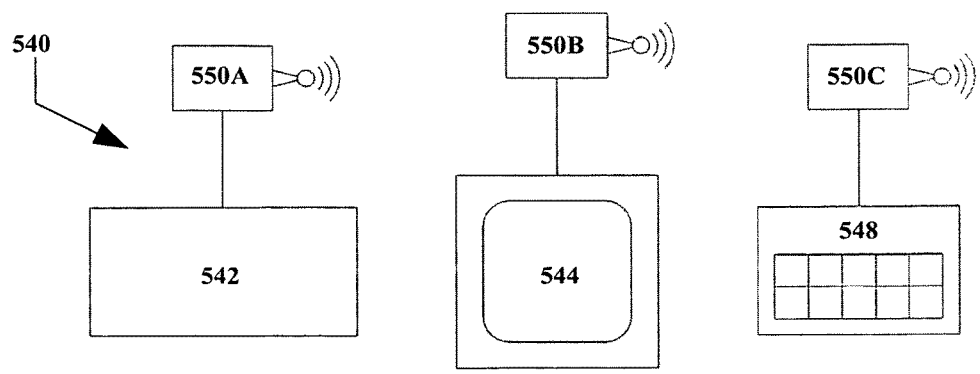
FIG. 5 shows yet another example embodiment of an apparatus for targeted interactive notification according to the present invention.

For example, FIG. 5 shows an arrangement wherein certain elements of an apparatus 540 according to the present invention are, or at least may be, physically or otherwise distinct.

The apparatus 540 shown in FIG. 5 includes a processor 542, a prompter 544, and an inputter 548 (which as noted previously may serve as a confirmer).

In addition each of the processor 542, prompter 544, and inputter 548 is in communication with a communicator 550A, 550B, and 550C respectively. Thus, each of the processor 542, prompter 544, and inputter 548 (and the respective communicators 550A, 550B, and 550C therefor) may be considered as independent devices. For example, the arrangement in FIG. 5 might represent a television as the prompter 544, a set-top box having the processor 542, and a cell phone, wireless remote, etc. having a keypad as the inputter 548.

In such an arrangement as that described immediately above for FIG. 5, the processor 542 in the set-top box might determine that a trigger is present for a therapeutic event, for example that it is 6:00 PM and thus it is time for a subject (presumably one watching or thought to be watching the television) to administer a glaucoma medication. The prompter 544 in the form of the television screen might then display a text message, graphic, etc. advising the subject of the need to administer the medication. The subject could then confirm receipt of the prompt, and/or confirm that the medication had been administered, by entering data on the keypad serving as the inputter 548. Though the individual processor 542, prompter 544, and inputter 548 are not necessarily part of the same device, nor necessarily wired together or otherwise directly connected, the processor 542, prompter 544, and inputter 548 may still serve collectively as an apparatus 540 according to the present invention (e.g. by communicating via the associated communicators 550A, 550B, and 550C therefor).

Thus, it will be understood that although an apparatus according to the present invention may be integrated into a single device, such as a cell phone, an apparatus according to the present invention also include elements that are physically and/or otherwise separate. Moreover, certain elements may be integrated into one device, while other elements are separate. For example, a sensor might be disposed in a smart watch or other wrist-mounted device, or in or on a container of medication, while the remaining elements (e.g. processor, prompter, etc.) may be incorporated into a cell phone or other device. The present invention is not particularly limited with regard to the form of an apparatus therefor, and arrangements other than those described above may be equally suitable.

Figure 6:
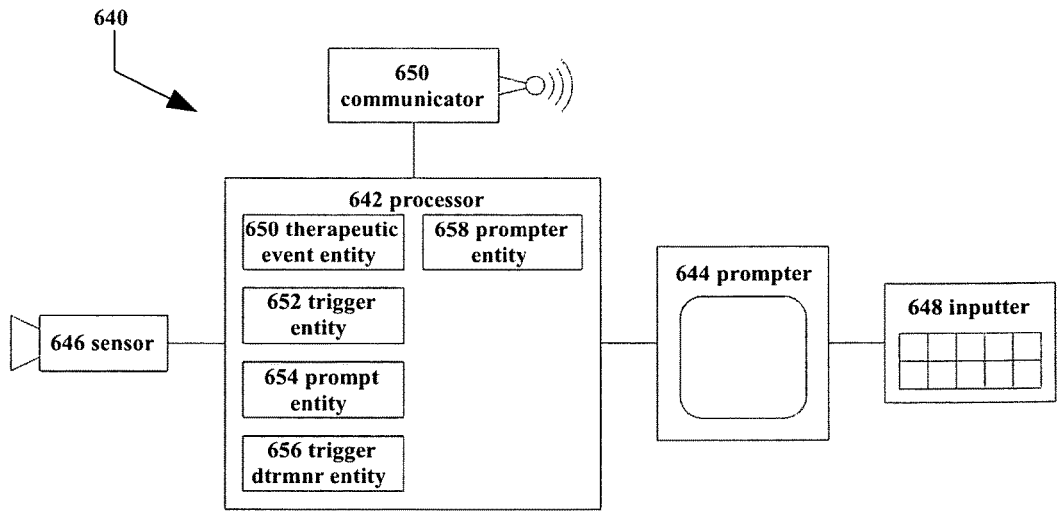
FIG. 6 shows an example embodiment of an apparatus for targeted interactive notification according to the present invention, indicating data entities instantiated on a processor therefor.

Now with reference to FIG. 6, although certain embodiments of an apparatus according to the present invention may utilize hardware dedicated to the functions thereof, the present invention may also include data and/or executable instructions instantiated on more general-purpose processors and/or other hardware. For example, the example embodiment in FIG. 6 shows an arrangement at least somewhat similar to that of FIG. 4, with an apparatus 640 having a processor 642, a prompter 644, a sensor 646, an inputter 648, and a communicator 650. Such hardware components have been described previously herein. However, rather than necessarily requiring dedicated hardware, arrangements such as that shown in FIG. 6 may form the present invention at least partly using data entities, e.g. readable data and/or executable instructions. The example in FIG. 6 shows an arrangement wherein data entities may be disposed on non-dedicated hardware, including but not limited to hardware such as a cell phone, tablet, smart watch, television, personal computer, head mounted display, etc.

For the embodiment shown in FIG. 6, the processor 642 has disposed thereon several data entities: a therapeutic event entity 650, a trigger entity 652, a prompt entity 654, a trigger determiner entity 656, and a prompter entity 658. The data entities may be stored information adapted to be read from, written to, etc. by the processor to inform some task and/or to record some task, may be executable instructions adapted to perform some task when executed by the processor, or may be other data.

The therapeutic event entity 650 is adapted to provide information regarding a therapeutic event. For example, a therapeutic event entity 650 may include data defining and/or describing some therapeutic event, such as administration of a medication.

The trigger entity 652 is adapted to provide information regarding a trigger for a therapeutic event. To continue the example above, a trigger entity 652 may include a time at which a therapeutic event is to be executed, and/or a time at which a prompt for the therapeutic event should be delivered.

It is noted that the present invention does not necessarily include a "condition entity" (though such would not necessarily be prohibited). The condition, as previously described, may be some parameter such as temperature. For an arrangement wherein, for example, the trigger entity refers to a specific temperature at which a therapeutic event is to be executed, such an arrangement may be sufficient absent some dedicated entity; the parameter or parameters may, and typically are, sufficient unto themselves (e.g. as features of an environment such as time, temperature, etc).

The prompt entity 654 is adapted to provide information regarding the content and/or delivery of a prompt for a therapeutic event. Again following the example above, a prompt entity 654 may include reminder information to administer the medication, the form that the information is to take (text, image, video, etc.), the manner by which the information is to be delivered (cell phone display, text message. television crawl feed, etc.).

The trigger determiner entity 656 is adapted to determine whether a trigger for a therapeutic event is satisfied. Typically though not necessarily the trigger determiner entity 656 will include at least some executable instructions adapted to make the relevant determination. Also typically though not necessarily the trigger determiner entity 656 may read from, communicate with, and/or otherwise interact with the therapeutic event entity 650 and/or the trigger entity 652. Also, the trigger determiner entity 656 may write to, communicate with, and/or otherwise interact with the prompter entity 658 to as to instruct delivery of the prompt if the trigger determiner entity 656 determines that the trigger is satisfied.

The prompter entity 658 is adapted to deliver a prompt related to a therapeutic event (if the trigger determining entity 656 determines that the trigger for that therapeutic event is satisfied). Again continuing the example above the prompter entity 658 may include executable instructions for outputting a text message reminder to administer a medication, for producing an animation reminder therefor, for producing a crawl feed on a television screen, etc. The prompter entity 658 may communicate with the prompt entity 654, for example receiving information regarding the form, destination, etc. of the prompt from the prompt entity 654.

Data entities may communicate with elements other than data entities disposed on the processor 642. For example, the trigger determiner entity 656 may communicate with the sensor 646 to receive data regarding whether trigger is satisfied. As a more concrete example, for a therapeutic event relating to administration of insulin in response to blood sugar levels, the trigger determiner entity 656 might communicate with a sensor adapted to determine the blood sugar level of a subject. Similarly, a prompter entity 658 may communicate with a sensor 646 to determine a location of a subject to whom a prompt is to be delivered, etc.

It is emphasized that the preceding descriptions of the therapeutic event entity 650, trigger entity 652, prompt entity 654, trigger determiner entity 656, and prompter entity 658 are examples only, and other arrangements may be equally suitable.

In particular, although for the arrangement shown in FIG. 6 all of the data entities 650, 652, 654, 656, and 658 are disposed on a single device, for other embodiments data entities may be divided amongst multiple processors 642, multiple devices, etc.

Figure 7:
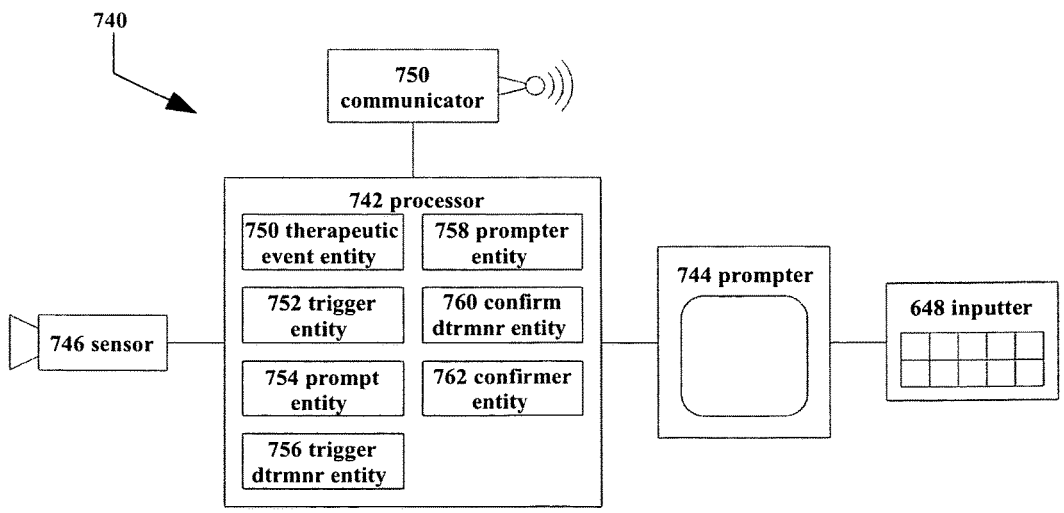
FIG. 7 shows an example embodiment of an apparatus for targeted interactive notification with confirmation according to the present invention, indicating data entities instantiated on a processor therefor.

Referring now to FIG. 7, as previously described the present invention may be adapted, but is not required to be adapted, to enable confirmation of a prompt and/or confirmation of a therapeutic action. The example arrangement in FIG. 7 is so adapted. Therein, an apparatus 740 is shown with a processor 742, a prompter 744, a sensor 746, an inputter 748, and a communicator 750. A therapeutic event entity 750, trigger entity 752, prompt entity 754, trigger determiner entity 756, and prompter entity 758 are instantiated on the processor 742.

In addition, a confirmation determiner entity 760 and a confirmer entity 762 are also disposed on the processor 742.

The confirmation determiner entity 760 is adapted to determine whether a prompt has been received, and/or whether a therapeutic event has been executed. Typically though not necessarily the confirmation determiner entity 760 will include at least some executable instructions adapted to make the relevant determination. Also, the trigger determiner entity 762 may write to, communicate with, and/or otherwise interact with the confirmer entity 762 to as to instruct delivery of the confirmation if the confirmation determiner entity 760 determines that the prompt has been received, and/or that the therapeutic event has been executed.

The confirmer entity 762 is adapted to deliver a confirmation that a prompt has been received, and/or to deliver a confirmation that a therapeutic event has been executed (if the confirmation determiner entity 762 determines that the prompt has been received, and/or that the therapeutic event has been executed). It is noted that the confirmer entity is not required to send a confirmation externally, or to any particular destination; for at least certain embodiments a confirmation might simply be recorded to a hard drive or other data store, or noted and retained within the processor, etc. However, sending a confirmation to an external destination also is not excluded, and confirmations may be sent for example to external databases, to health professionals, to friends or caretakers, etc.

Furthermore, confirmation may take the form of a message to the subject of the prompt himself or herself. For example, for an arrangement wherein a cell phone or other portable device sends a prompt, that device might itself display to the subject confirmation, e.g. by turning on an LED or other telltale, by displaying a confirmation message, etc. Potentially but not necessarily such subject-directed confirmation may be combined with other confirmation, for example the subject might receive a message so that the subject is aware that the administration of medication has been confirmed and logged by the apparatus, etc.

In addition, it may for at least some embodiments be possible for a confirmation to be created, sent, etc. without the use of either or both of a confirmation determiner entity 760 and a confirmer entity 762. For example, a confirmation may be sent through the actions of the subject of the person receiving the prompt (or some other person, system, etc.), e.g. by being keyed in on an inputter 748. In such instance, the confirmation may not utilize (and/or may not require the presence of) a confirmation determiner entity 760 or a confirmer entity 762, since the subject may determine whether the prompt has been received and/or whether the therapeutic event has been executed, and the subject may likewise deliver the confirmation thereof. Confirmation thus might be enabled by an arrangement such as shown in FIG. 6, as well.

Figure 8:
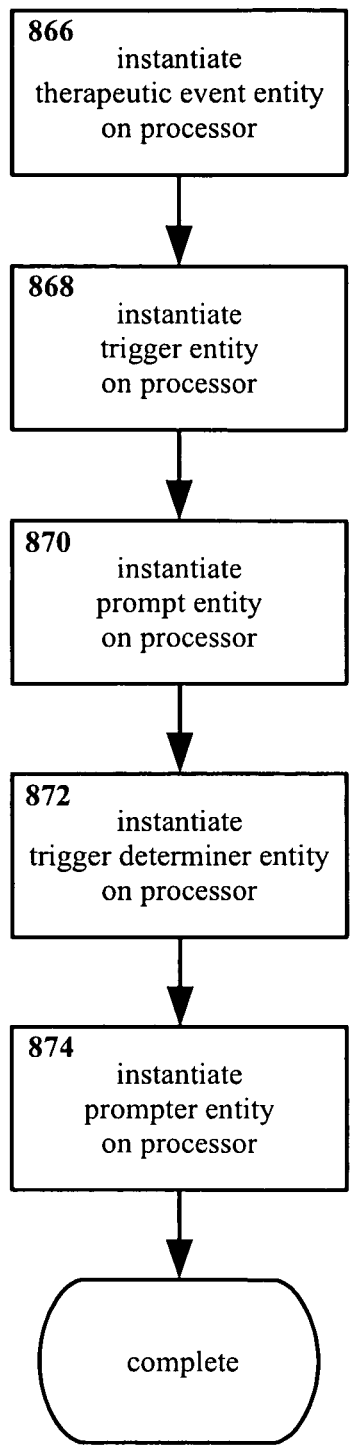
FIG. 8 shows an example embodiment of a method for establishing targeted interactive notification according to the present invention.

Turning now to FIG. 8, therein is shown an example method for establishing on a processor, and/or on a device including a processor therein, a capability for targeted interactive health status notification according to the present invention.

In the example method of FIG. 8, a therapeutic event entity is instantiated on a processor 866. The therapeutic event entity includes data and/or executable instructions adapted for establishing a therapeutic event. A therapeutic event entity according to the present invention has been previously described herein.

The present invention is not particularly limited with regard to the source of the therapeutic event entity and/or data and/or executable instructions thereof. Typically, though not necessarily, the translation determiner might be instantiated 866 onto the processor from a data store such as a hard drive, solid state drive, etc., or from a communications link such as wifi, a wired connection, etc. However, these are examples only, and other arrangements may be equally suitable. (These comments likewise apply to similar steps in FIG. 8 and FIG. 9 herein, in that the present invention is not particularly limited with regard to sources for information associated therewith.)

Continuing in FIG. 8, a trigger entity is instantiated on the processor 868. The trigger entity includes data and/or executable instructions adapted for establishing a trigger. A trigger entity according to the present invention has been previously described herein.

A prompt entity is instantiated on the processor 870. The prompt entity includes data and/or executable instructions adapted for establishing a prompt. A prompt entity according to the present invention has been previously described herein.

A trigger determiner entity is instantiated on the processor 872. The trigger determiner entity includes data and/or executable instructions adapted for determining the presence of a trigger for a therapeutic event. A trigger determiner entity according to the present invention has been previously also described herein.

A prompter entity is instantiated on the processor 874. The prompter entity includes data and/or executable instructions adapted for delivering a prompt. A prompter entity according to the present invention has been previously described herein.

Although FIG. 8 shows the method therein as being complete following step 874, it is emphasized that the method in FIG. 8 is an example only. Other steps, other functions, etc. may be incorporated into the method, and/or other methods may be executed in combination with the method according to the present invention. For example, for at least some embodiments other executable instructions and/or data may be instantiated onto the processor, whether related to the method steps described herein or otherwise.

Figure 9:
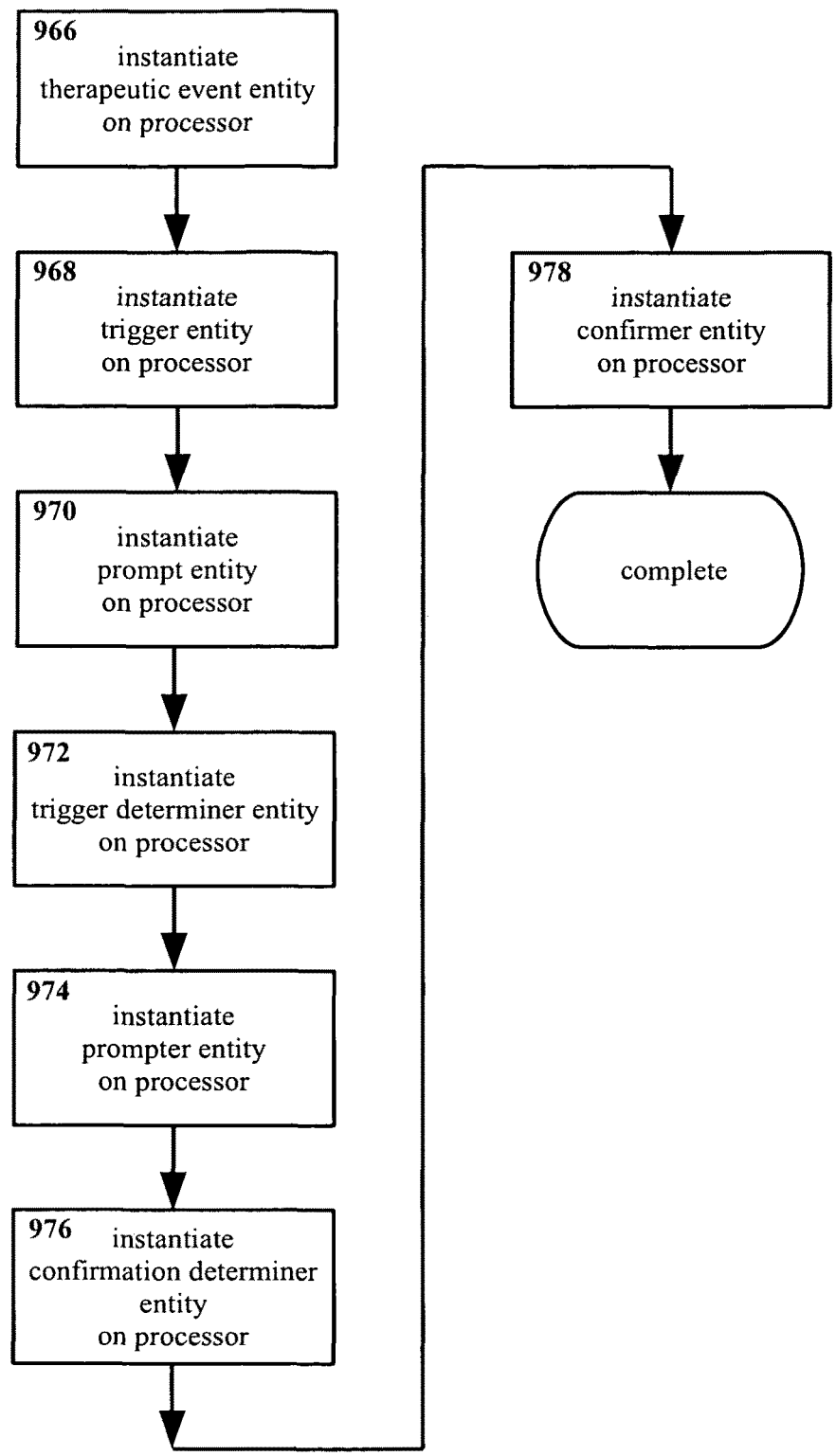
FIG. 9 shows an example embodiment of a method for establishing targeted interactive notification with confirmation according to the present invention.

Referring now to FIG. 9, therein is shown an example method for establishing on a processor, and/or on a device including a processor therein, a capability for targeted interactive health status notification with confirmation according to the present invention.

In the example method of FIG. 9, a therapeutic event entity is instantiated on a processor 966. A trigger entity also is instantiated on the processor 968. A prompt entity is instantiated on the processor 970. A trigger determiner entity is instantiated on the processor 972. A prompter entity is instantiated on the processor 974.

Continuing in FIG. 9, a confirmation determiner entity is instantiated on the processor 976. The confirmation determiner entity includes data and/or executable instructions adapted for determining whether a prompt has been received, and/or for determining whether a therapeutic event has been executed. A confirmation determiner entity according to the present invention has been previously described herein.

A confirmer entity is instantiated on the processor 978. The confirmer entity includes data and/or executable instructions adapted for delivering a confirmation that a prompt has been received, and/or that a therapeutic event has been executed. A confirmer entity according to the present invention has been previously described herein.

Although FIG. 9 shows the method therein as being complete following step 978, it is emphasized that the method in FIG. 9 is an example only. Other steps, other functions, etc. may be incorporated into the method, and/or other methods may be executed in combination with the method according to the present invention. For example, for at least some embodiments other executable instructions and/or data may be instantiated onto the processor, whether related to the method steps described herein or otherwise.

At this point it may be illuminating to describe the appearance and/or function of certain particular embodiments of the present invention, and/or portions of the embodiments. It is emphasized that the present invention is not limited only to such specifically-described embodiments.

One example embodiment of an apparatus according to the present invention might include data and/or executable instructions instantiated on a portable and/or wearable electronic device such as a smart phone, tablet, smart watch, head mounted display, etc. In such an arrangement, all or substantially all elements of an apparatus according to the present invention might be incorporated therein, and all or substantially steps of a method according to the present invention might be performed thereby. For example, a smart phone may include a processor, a screen and speaker that may serve as a prompter, one or more sensors (motion sensors, a camera, etc.), a keypad, touch screen, microphone, etc. that may serve as an inputter, wireless telephone and/or data links that may serve as a communicator, etc. Such an arrangement has been referred to previously herein.

For such an arrangement, with an integrated portable device such as a smart phone, consider as an example administration of a glaucoma medication, the medication being in the form of eye drops dispensed from a squeeze bottle. Administration of the glaucoma medication would, in this example, be the therapeutic event. The trigger might be, or at least might include, a time; smart phones frequently include therein internal chronometers (e.g. integrated into the CPU), thus enabling determination of whether the current time satisfies the trigger. The prompt could then be a visual message shown in the smart phones display screen, which could be displayed to advise a subject such as the user of the smart phone that it is time to administer the glaucoma medication. Confirmation might for example include a key press, voice input, etc. Confirmation could be logged or forwarded to some other device, so as to provide a record that the glaucoma medication was administered, the time that the glaucoma medication was administered, etc.

Such an arrangement may be targeted to an individual patient with glaucoma, and/or to his or her particular medical status, specific prescriptions, and so forth. Furthermore, such an arrangement also enables data logging and/or other confirmations that the glaucoma medication has been taken, and/or has been taken on time. Such features may be useful, at least because for certain medications and medical issues carefully following a treatment regimen may be vital to successful management or cure. Notably, glaucoma is one such. Glaucoma typically is asymptomatic in the short term; persons with glaucoma may experience no pain, or other noticeable difficulties. Glaucoma is also frequently readily treatable, with regular doses of medication allowing many persons with glaucoma to remain mostly or entirely asymptomatic. However, missing or delaying doses of glaucoma medication can have extremely serious medical consequences, ultimately including severe loss of eyesight, but those consequences are often sufficiently delayed that they may not be useful as reminders to take the medication, or to take the medication on time.

Thus, for at least certain health concerns, scrupulous adherence to a prescribed regimen of medical treatment may be extremely effective, while deviations from such a regimen may result in severe health consequence. Glaucoma, while one such health concern, is an example only, and other therapeutic events may be of similar concern.

Another example embodiment of an apparatus according to the present invention might include at least some elements thereof distributed to different physical devices. For example, one or more motion sensors might be disposed in a wearable wrist device (e.g. a pedometer, exercise sensor, smart watch, etc.) while other elements such as the processor, prompter, etc. could be in another device such as a smart phone, tablet, laptop or desktop computer, etc. Note that the inclusion of sensors in one device does not preclude the inclusion of sensors in another device; a wrist device might include accelerometers, gyroscopes, etc., while a smart phone providing a processor might also incorporate similar sensors. For at least certain embodiments, placement of sensors in certain locations, for example on the wrist or arm, may be useful in sensing motions that are sufficiently specific and/or characteristic as to identify certain activities, including but not limited to therapeutic events. For example, hand and arm motions for administering eye drops (e.g. as glaucoma medication) may be sufficiently characteristic for such purposes. More regarding characteristic motions and other activities is described later herein.

Yet another example of an apparatus according to the present invention might include sensors might distributed on a specialized device, including but not limited to a medical device. For example, sensors for detecting motion, contact, pressure, etc. might be disposed on a medication container, and/or on some fitting attached to the medication container. As a more concrete example, a deformable collar with accelerometers, gyroscopes, deformation sensors, etc. might be engaged with a squeeze bottle for administering eye drops such as glaucoma medication. For such an arrangement, characteristic motions of the bottle as a subject lifts, tilts, and/or squeezes the bottle to apply a drop to his or her eye might be used to confirm administration of the medication. As noted above with regard to wrist-mounted sensors, the use of such a collar would not necessarily preclude the use of some other device, such as a smart phone, to provide elements such as a processor, etc.

Still another example of an apparatus according to the present invention may include prompters that are physically distinct from at least some other elements. For example, a television, PC monitor, or other display screen might be utilized as a prompter. For a television, a processor (if not present in the television) might take the form of a set-top box. For a PC or other device (including certain televisions) a processor suitable for the present invention may be present therein. Regardless, the television, monitor, etc. may deliver a prompt to a user, even though the processor may be in a distinct device.

It is noted that for each such example, although presented in terms of hardware, a method according to the present invention likewise might be executed on such hardware.

For example, a cell phone might establish a therapeutic event, trigger, and prompt thereon, determine whether the trigger is present, prompt a subject, and/or confirm or accept confirmation of the prompt and/or execution of the therapeutic event (such as administration of a medication), as an integrated device (e.g. with executable instructions for carrying out the method instantiated on the smart phone processor).

Similarly, sensors disposed on a wrist band might determine whether a trigger is present, whether a therapeutic event has been executed (whether a medication has been administered, etc.), and so forth. Other steps of the method might be carried out on the wrist band, or on another device such as a smart phone, tablet, PC, etc.

Likewise, sensors disposed on a medication container might determine whether a therapeutic event has been executed (e.g. by sensing the manipulation of the medication container), etc. Other steps of the method again might be carried out on the medication container (or device engaged therewith), or on another device such as a smart phone, tablet, PC, etc.

Further, prompts might be delivered on a television screen, monitor, etc., with other steps potentially being carried out on other devices such as a set-top box, computer CPU, etc.

A more detailed explanation of certain steps and features of the present invention now follows, as referenced earlier herein.

With regard to therapeutic events, the present invention may encompass a large range of potential therapeutic events. Notably, a therapeutic event according to the present invention may include administration of a medication. Substantially any medication might be administered as a therapeutic event, including but not limited to pills, capsules, liquids, and other oral medications, injections, dermal patches, eyedrops, topical applications (ointments, etc.), vapors (such as an asthma inhalant), etc. Other forms of medication may be equally suitable.

In addition, therapeutic events may include non-medication events. For example, a therapeutic event may include utilizing a medical device, such as wearing an orthodontic retainer or a carpal tunnel brace. As another example, a therapeutic event may include acquiring data, for example conducting a measurement (either with an automatic system, as performed by a person, etc.). More concrete examples might include measuring blood pressure, measuring heart rate, measuring body temperature, etc. However, it is emphasized that acquiring data is not limited only to data regarding a human subject. Measuring air temperature, pollen count, ultraviolet intensity, etc. may also be equally suitable. Moreover, data acquisition is not limited to testing or measurement, and may include querying patients or other subjects for comments, obtaining information from databases, and other data acquisition approaches.

As yet another example, therapeutic events may include activities or behaviors, including but not limited to activities or behaviors to be performed by, or to be avoided by, a patient or other subject. As more concrete examples, a subject might be expected to perform some exercise, eat or drink, sleep, to take a rest break from performing some activity (such as typing for an individual prone to carpal tunnel syndrome), etc. Conversely, a subject might be expected to avoid direct sunlight (for example if taking a medication increasing ultraviolet sensitivity), to refrain from operating heavy machinery, to avoid lying down (for example to avoid complications from certain medications wherein position, internal pressure, etc. may play a role), or even to leave an area with high levels of pollutants (for example going indoors during high-ozone periods if a subject is prone to asthma).

For at least some embodiments, a therapeutic event may include a subject being made aware of a risk, benefit, etc. For example, an individual prone to asthma might be made aware of an increased risk of asthma attacks at high elevations, a diabetic might be made aware of unusually high sugar content in certain foods, a person with allergies might be made aware of a high pollen count, etc. In such cases the consideration of information may itself constitute a therapeutic event, regardless of whether any visible physical action is to be performed.

It is noted that therapeutic events are not necessarily limited to personal events. For example, a subject might be advised of the need to administer a medication to some other subject (such as a parent administering a medication to a young child).

The present invention is not particularly limited as to what usages of medical devices, measurements, exercises, behaviors, etc. may be suitable as therapeutic events. Furthermore, the present invention is not limited only to such therapeutic events as described herein.

Now with regard to triggers and conditions therefor, the present invention may encompass a wide range of potential triggers, and a wide range of conditions for such triggers. As previously described, a condition in the present invention includes parameters that may be relevant to a health matter, while a trigger includes some level, behavior, pattern, etc. in a phenomenon that may make a therapeutic event necessary and/or desirable.

For example, conditions may include factors such as time, location of a subject, location of other persons, objects, or phenomena, etc. Conditions may also include bio-information and/or medical parameters, such as a subject's blood pressure, blood sugar level, blood oxygen level, pulse, body temperature, etc. Conditions may include environmental conditions, such as air temperature, air pressure, humidity, pollen count, ultraviolet light level, ozone level, etc.

Conditions also may include properties of persons, objects, etc. For example, for a person with a peanut allergy the composition of foods nearby—i.e., the presence and/or concentration of peanut products therein—may be of relevance to his or her health.

Conditions may also include the presence or absence of persons, animals, objects, etc. For example, the presence of a cat could potentially be relevant to the health of persons with allergies to cats, persons with asthma, etc. Similarly, the presence of bees might be relevant to the health persons sensitive to bee stings.

Conditions further may include behaviors, whether of the person for whom the health matter is of potential concern or of other persons, animals, etc. For example, whether a person is standing, sitting, or lying down may be relevant to the performance of certain medications (such as some glaucoma medications). Likewise whether a person is jogging or otherwise exercising, or has recently, or appears to be preparing to do so, may be relevant at least for the performance of certain medications. Whether a person nearby is smoking may be relevant to the health of a person sensitive to second-hand smoke (such as persons with asthma).

The present invention is not particularly limited with regard to what conditions may be considered, and/or to how those conditions may be determined.

Now with regard to triggers, as previously noted triggers may include states, levels, patterns, etc. within relevant conditions, wherein whether a particular trigger is satisfied may serve as a determination as to whether a therapeutic event is necessary or desirable. It may be said that a trigger is the threshold at which a particular therapeutic event is to be performed.

It will be understood that triggers may depend to at least some degree on the therapeutic condition in question. Likewise, triggers may depend to at least some degree on the condition in question. For example, with regard to time as a condition, a trigger might be the current time, or some relative time such as how long some condition has persisted (e.g. how long a subject has been asleep), how long since a medication was last administered, etc.

Conditions and triggers may to at least some degree be interrelated. For example, if the trigger for taking a medication (a therapeutic event) is the amount of time elapsed since the last dose, the trigger depends both on time and on previous behavior (that is, when the last does was administered).

Returning to examples of triggers, for bio-information triggers may include consideration of the level of some parameter, such as the magnitude of a subject's blood pressure, whether the blood pressure exceeds some maximum or is below some minimum, the degree of variation in blood pressure over time, etc. Likewise, for certain forms of bio-information patterns may be considered, such as the "shape" of a heartbeat (e.g. the waveform generated by an electrocardiogram), and/or the change in such shape, as well as features such as the heart rate itself.

Now with respect to prompts, a prompt is a vehicle by which a therapeutic event is "invoked". That is, a prompt is the means by which a therapeutic event is caused or suggested to be executed.

Typically a prompt may include delivery of information to a subject, delivery of instructions to a subject, execution of some test, measurement, etc. to obtain information, or querying of a subject to obtain information. However, the present invention may accommodate other options as well. For example, under certain conditions a prompt might include establishing a communication link, for example between a patient and a health care provider.

As has been stated, prompts are not necessarily directed towards the subject for whom the health matter is directly applicable. For example, a prompt might be sent to inform emergency services that a subject known to have a heart condition is experiencing potentially dangerous heart activity, or a prompt might be sent to a parent to advise him or her regarding the administration of medication to a young child.

In addition, a prompt may define the manner by which a therapeutic event is invoked. That is, for example considering delivery of instructions to a subject, a prompt may include therein definitions for and/or a description of how those instructions are to be delivered to the subject. As a more concrete example, considering as a therapeutic event the administration of medication, and a prompt including instructions to administer the medication, the prompt might include not only the instructions to the subject but also an indication that the instructions are to be delivered as a text message, as an animation, as a voice output, etc. Similarly, the prompt might include an indication that the instructions are to be delivered via a smart phone, via a television screen, etc. For certain embodiments the manner by which a therapeutic event is prompted may be variable or conditional, for example a prompt might be delivered as an animation to a smart phone display if it is known, determined, suspected, etc. that the subject has a smart phone on and nearby, but might be delivered as a text crawl to a television screen if it is known, determined, suspected, etc. that the subject is watching television. Likewise, a prompt might not be delivered at all if it is known, determined, suspected that the prompt itself might present a health risk, e.g. by distracting a subject who is driving a vehicle.

A prompt may be detailed and/or complex, for example a comprehensive description of heart behavior for the past 24 hours. However, a prompt also may be extremely simple. For example, a medication container or device engaged therewith might include an LED or other telltale, wherein the LED is normally off but turns on as a prompt to take a medication (or is on but changes color, etc.). Similarly, a prompt delivered using a cell phone might simply be a graphic that appears on the display thereof, a brief audible message, a vibration, etc.

Simple prompts may be useful for at least certain embodiments. For example, for a patient taking eye medication, it may be more likely that such a patient has vision that is or may become at least somewhat impaired. Likewise, increasing age may correspond in at least some cases with a combination of reduced visual acuity and increased need for medication. A prompt such as a colored or flashing LED may be readily noticed as compared, for example, with printed instructions, particularly such instructions as may utilize in fine print to compensate for limited space (e.g. a label on a medication container).

However, complex and/or sophisticated prompts may also be equally suitable, and the present invention is not particularly limited with regard to the complexity of the prompt (nor likewise with regard to the complexity of the therapeutic event, condition, trigger, confirmation, etc.).

Now with consideration to confirmations, a confirmation is a response to a prompt, for example confirming receipt of the prompt (thus perhaps implicitly confirming knowledge of information therein, etc.) and/or confirming execution of a therapeutic event referred to in a prompt.

Confirmations may be manual, that is, consciously or deliberately sent by a user in response to a prompt. For example, a user receiving a prompt by text message to administer a medication might send a text message (or some other message) in reply to indicate that the prompt was received, that the medication was administered, etc. Manual confirmations may be useful at least insofar as manual confirmations enable active user participation. That is, a user who is deliberately sending a confirmation may, if necessary and/or desirable, tailor a message and/or destination thereof to special circumstances. For example, a user sending a confirmation to a prompt to administer a medication might describe difficulties in administering the medication, might record what he or she was doing when the medication was administered, might describe side effects thought to be associated with the medication, might inquire for additional information or instructions, etc.

However, confirmations also may be partially or entirely automated. For example, sensors in a smart phone, a smart watch, a sensored wrist band, a medication container, etc. might automatically determine whether a therapeutic event has been executed. As a more concrete example, considering administration of a medication as a desired therapeutic event, sensors in the medication container might automatically indicate whether the medication is administered, for example by sensing characteristic motions, manipulations, etc. of the container that are associated with administration of the medication. Automatic confirmations may be useful at least insofar as automatic confirmations enable confirmation of a therapeutic event without requiring the attention and time of a user. If a confirmation is generated and transmitted automatically, then a user cannot forget to send the confirmation, send the confirmation incorrectly, send the confirmation to the wrong destination, etc. Likewise, a user does not have to devote time, concentration, or effort to sending a confirmation if the confirmation is sent automatically.

As previously noted with regard to prompts, confirmations likewise may be either complex or simple. Confirmations may for example utilize sophisticated approaches such as image analysis for object recognition, action recognition, etc. However, confirmations also may be extremely simple.

Continuing with the example regarding images, simple confirmations might include, but are not limited to, using an imager to detect an LED, possibly an LED with a particular color or blinking or otherwise changing in some pattern, using an imager to read a bar code, QR code, etc. Such an LED, bar code, QR code, etc. might be disposed on a medication container or therapeutic instrument, for example. It is noted that certain recognizable features suited for confirmation may already be available, for example medication containers and medical instruments may already have bar code markings thereon, so that the present invention might utilize such markings without any modifications to existing medication containers, instruments, etc. However, arrangements wherein dedicated features may be utilized are not excluded from the present invention.

Notably, a confirmation according to the present invention may also be negative. That is, the confirmation may include a reply indicating that some event did not take place, etc. For example, a user receiving a prompt to administer a medication at a particular time might send a confirmation message indicating that the medication was not administered at that time, perhaps also indicating that the medication has already been administered, that the medication is unavailable, that conditions exist such that administering the medication is impossible or undesirable, etc. Thus, although a confirmation may typically be considered as a vehicle for indicating that an action has taken place, the present invention includes arrangements wherein a confirmation indicates that some action has not taken place.

It is noted that at least certain steps in a method according to the present invention may carry information, medical or otherwise, that may be of value beyond the immediate therapeutic action associated therewith. For example, a common concern in determining the effectiveness and/or side effects of medications, medical devices, therapies, etc. is lack of data regarding such matters as when the medication (for example) was administered, what the user was doing at the time, what the user was doing before and after, what ambient conditions were present, what side effects occurred and when, etc. In certain cases, such as hospital care, at least some such information may be obtained through direct observation, control of the environment, and so forth. However, medical care, including but not limited to the administration of prescription medications, frequently occurs outside of hospitals and away from medical supervision.

The present invention enables such data collection even in uncontrolled environments, for example for patients taking medication at home. In the present invention, a prompt is sent; that prompt typically includes well-defined information: a subject is to administer a specific medication at a specific time in a specific dose, possibly under specific conditions, etc. For at least certain embodiments of the present invention, a confirmation likewise may be sent, again typically with well-defined information: what medication in fact was administered, at what time, at what location, in what dose, under what conditions, with what side effects, with the patient in what condition (body position, heart rate, blood oxygen level, etc.), etc. Such detailed information, regarding either or both the prompt and the confirmation, may be useful at insofar as informing activities including but not limited to medical research.

Collection of such data may be incorporated seamlessly into the present invention, by selections regarding such features as the prompt and (if present) the confirmation. For example, as noted a prompt may include information regarding where the prompt is to be delivered (e.g. a smart phone, a television set, a PC monitor, etc.), how the prompt is to be delivered (e.g. as text, as image data, etc.), and/or what content the prompt may include therein (e.g. information for the subject, instructions to the subject, a time stamp indicating the time the prompt was sent, etc.). A prompt (or at least some portion of information therein) may therefor readily be sent to both a subject and a database, researcher, computer system, etc., while remaining within the scope of the present invention. Alternatively, one prompt might be sent to one subject such as a patient, while another prompt is sent to another subject such as a physician, a data file, etc. Likewise, confirmations and some or all information therein might be sent to one subject (e.g. a patient), and one or more other subjects (a caregiver, a friend, a medical research database, etc.) in addition to or instead of the patient.

In addition, it is noted that the present invention is not limited only to collecting information in support of determining the presence of a trigger, and/or confirming the receipt of a prompt, and/or confirming execution of a therapeutic event. As has been previously described, information may be so collected, and such information may also be applied for other purposes including but not limited to health related applications. However, additional information may be collected, regardless of whether such information is directly related to determining the presence of a trigger, and/or confirming the receipt of a prompt, and/or confirming execution of a therapeutic event.

For example, given a capability of the present invention to determine whether a trigger is present, such capability may be utilized for additional data collection. As a more concrete example, if an embodiment of the present invention considers the blood sugar level of a subject as part of determining a trigger (e.g. for a case wherein the trigger is satisfied when the subject's blood sugar exceeds some maximum or falls below some minimum), some capability to determine the subject's blood sugar level presumably may be available as part of the present invention (including but not limited to sensors that monitor the subject's blood sugar level). Under such circumstances, certain embodiments of the present invention may monitor, record, log, etc. the subject's blood sugar at intervals, substantially continuously, etc. Even if the data so obtained never satisfies a trigger condition, such data may be collected and/or transmitted to a database or other subject while remaining within the scope of the present invention.

Moreover, it is noted that the present invention is not limited to collecting such additional information only regarding conditions utilized by a trigger and/or a confirmation. To continue the above example, even if blood pressure and heart rate are not considered in determining whether a trigger is satisfied or whether a confirmation is sent, certain embodiments of the present invention may nevertheless record blood pressure, heart rate, etc.

Such additional data may be useful, at least for certain embodiments. For example, one difficulty in determining effectiveness, side effects, etc. for a therapeutic event such as administration of a medication is lack of information regarding when the medication was administered, how the mediation was administered, etc. The present invention may enable convenient collection of such information, potentially assisting in determination of the effectiveness and/or safety of medications, etc. Moreover, the present invention may collect such potentially useful information regardless of whether the information is immediately related to triggers, confirmations, etc. Such data collection may be particularly advantageous, for example, in cases wherein medications or other therapies are in initial testing, such as part of pharmaceutical research, etc.

Many factors may, for example, affect the safety and effectiveness of therapeutic events. For example, what a subject receiving medication eats and when, when a subject sleeps and in what position, what other medications (if any) the subject takes, in what does, and when, what environmental factors exist near the subject, what activities the subject engages in, etc. may potentially affect how well medications work, what side effects are present and how serious those side effects are, etc. Through collecting data on such factors, the present invention may enable control of variables without the use of a controlled test population (e.g. volunteers in prisons), and without either limiting the activities of the subjects or imposing problematic levels of record-keeping on the subjects (that is, subjects would not need to record their blood pressure or the ambient temperature if such data is already being recorded). Such factors may be utilized for triggers, confirmations, etc., but may also be of use when not so utilized.

It is noted that certain embodiments of the present invention may already incorporate sensors and/or sensor capabilities suited for supporting such data collection. For example, as noted the present invention may be implemented utilizing a device such as a smart phone. Smart phones typically include sensors such as imagers, audio sensors, accelerometers, gyroscopes, etc., and/or other sensors. Thus supplemental data capabilities as described above may in at least certain embodiments be implemented using capabilities already present (though the utilization of additional data collection capabilities, such as supplemental sensors, also is not excluded).

Ownership of data, regardless of whether such data is related to triggers, confirmations, etc., may remain with the source and/or subject thereof. That is, sharing information contained within a prompt or confirmation, or otherwise obtained, does not necessarily imply a transfer of ownership of the information, and the subject of such information (e.g. an individual patient) may retain some or all rights thereto. Information so shared or delivered might even be handled as a transaction, e.g. a company engaged in medical research regarding a drug or procedure might pay for the data on a per-prompt or per-confirmation basis (or using other arrangements such as a flat fee, monthly fee, etc.).

Information likewise may be anonymized by removal of certain data (e.g. cell phone numbers, names, electronic addresses, etc. that might be associated with some subject) so as to maintain privacy of subjects while still enabling collection of useful data. Similarly, information (including but not limited to prompts and confirmations) may be encrypted or otherwise protected from interception, for example to retain privacy, and/or may be code-stamped or otherwise identified (for example using some mathematical key or algorithm to demonstrate validity without necessarily making the data traceable to an individual) so to as to increase confidence that the information therein is valid rather than spurious or fraudulent.

These are examples only, and other approaches for handling and/or utilizing data within the scope of the present invention may be equally suitable.

Figure 10:
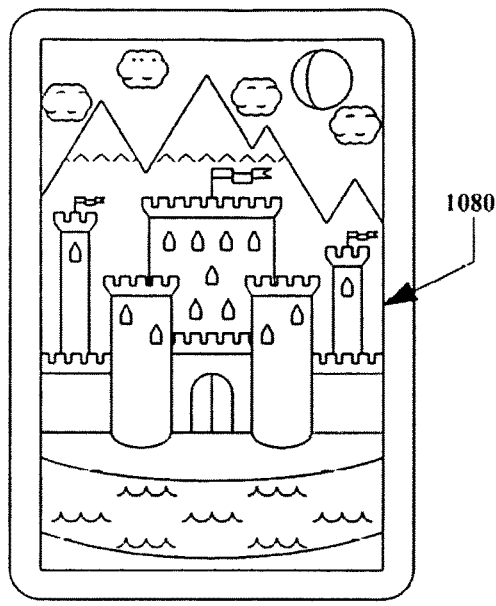
FIG. 10 through FIG. 13 show an example embodiment of a prompt according to the present invention.

Now with reference to FIG. 10, as has been stated previously the present invention is not particularly limited with regard to the content of a prompt, and/or the manner in which a prompt may display information, deliver instructions, etc. For at least certain embodiments, a prompt may be delivered in such fashion as to be contextually relevant and/or recognizable.

For example, consider an arrangement wherein a subject is to be prompted with instructions to take a glaucoma medication (i.e. the therapeutic event is for the subject to administer the medication). FIG. 10 shows an example arrangement wherein a prompt might be delivered in a fashion that is contextually relevant to glaucoma, and/or readily recognizable to a subject under treatment for glaucoma.

In the example of FIG. 10 (and in certain subsequent images) a screen image such as might be displayed on a cell phone is illustrated. As has been noted, certain embodiments of the present invention may utilize a cell phone, e.g. instantiating executable instructions adapted to execute a method according to the present invention on the processor thereof. However, it is emphasized that the present invention is not limited only to cell phones.

In FIG. 10, an image 1080 is shown displayed. The image 1080 is a baseline image, that is, the image is shown in a "normal" mode, i.e. without modification such as by a prompt according to the present invention.

Figure 11:
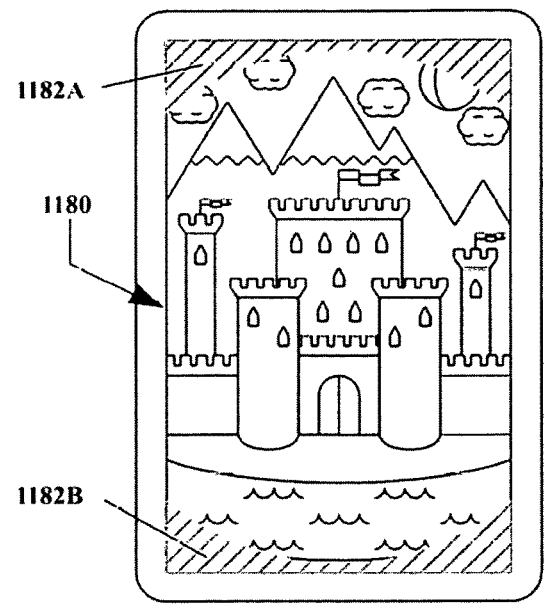

Now with reference to FIG. 11, as may be seen an image 1180 is again shown therein. The image 1180 in FIG. 11 is visibly at least somewhat similar to the baseline image 1080 shown in FIG. 10. However, as also may be seen in FIG. 11, two additional features, referred to herein as prompting features 1182A and 1182B, also are visible therein.

The prompting features 1182A and 1182B are adapted attract an attention of a subject, e.g. a subject viewing the image 1180. In the example arrangement shown in FIG. 11, the prompting features 1182A and 1182B are more particularly adapted to attract a subject's attention by obscuring the image 1180. Notably, the prompting features 1182A and 1182B obscure an extreme periphery of the image 1180, while leaving the majority of the image 1180 (including the central portion of the image) 1180 unobscured.

It is noted that glaucoma typically obscures a person's sight beginning at the periphery thereof. That is, some or all of the peripheral vision is lost first, while the central vision may remain unobscured. Thus, the arrangement shown in FIG. 11—wherein the periphery of an image 1180 is obscured by prompting features 1182A and 1182B—is to at least some degree similar to and/or evocative of the medical effects of glaucoma. For a subject with glaucoma, and for whom a therapeutic event is to administer a glaucoma medication, the prompting features 1182A and 1182B shown in FIG. 11 may therefor be considered to be contextually relevant to the subject's glaucoma. More generally, the prompt being delivered may be considered to be contextually relevant to the therapeutic event.

Figure 12:
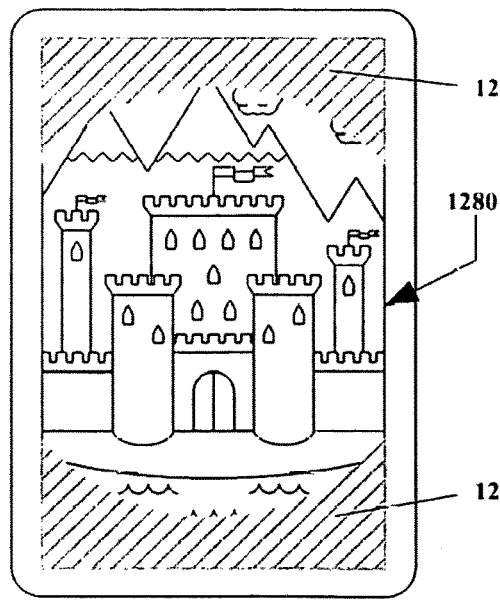

Turning now to FIG. 12, therein an image 1280 may be seen with prompting features 1282A and 1282B. The image 1280 and prompting features 1282A and 1282B may be seen to be at least somewhat similar to those in FIG. 11, however in FIG. 12 the prompting features 1282A and 1282B obscure a larger portion of the image 1280, thus at least arguably being more noticeable and/or more readily attracting a subject's attention.

Figure 13:
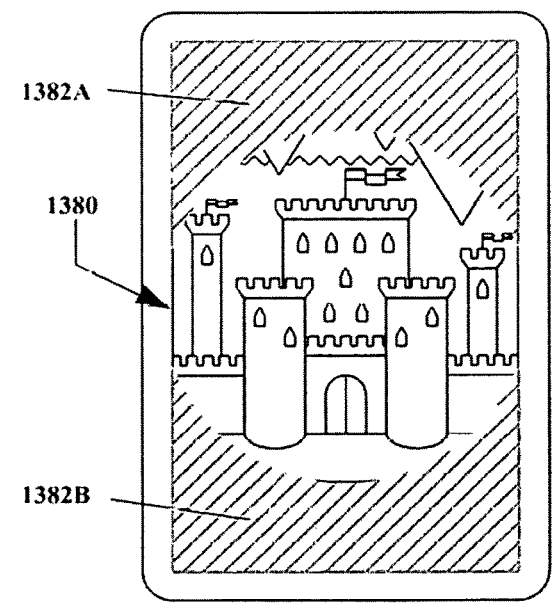

Similarly, in FIG. 13 therein an image 1380 may be seen with prompting features 1382A and 1382B. The image 1380 and prompting features 1382A and 1382B may be seen to be at least somewhat similar to those in FIG. 12, however yet again in FIG. 13 the prompting features 1382A and 1382B obscure a still larger portion of the image 1380, thus at least arguably being still more noticeable and/or still more readily attracting a subject's attention.

Considering FIG. 10 through FIG. 13 collectively as a time-sequence, it may be seen that the images shown therein are progressively obscured by the prompting features in a fashion resembling the progressive loss of eyesight associated with glaucoma. Thus, FIG. 10 through FIG. 13 may represent a prompting to a subject to administer a glaucoma medication, that prompting being contextually relevant at least insofar as the prompting to take the medication resembles the effect of the user not taking the medication. Moreover, if the subject does not administer the medication, the degradation of the image as time passes resembles the loss of the subject's eyesight over time. (Conversely, if the subject does administer the medication—e.g. a confirmation indicates that the therapeutic event has been executed—the prompting effects seen in FIG. 10 through FIG. 13 may be reversed, may terminate, etc.)

Contextually relevant prompting may be useful, at least insofar as in such case the prompt may be particularly functional by virtue of psychological impact. For example, a subject may less readily ignore or overlook a prompt that resembles or evokes a health problem from which that subject suffers (and/or may suffer by ignoring the prompt) than a more abstract prompt such as a simple icon, text message, etc. Also, a device displaying such images may become progressively more difficult to use with increasingly prominent prompt features displayed thereon, and/or with other contextually relevant prompting delivered to a subject therethrough. However, it is emphasized that the present invention is not limited only to contextually relevant prompting, and other arrangements may be equally suitable.

In addition, while the arrangement shown in FIG. 10 through FIG. 13 may illustrate a particular arrangement for contextually relevant prompting according to the present invention, the present invention is not limited only thereto. Other contextually relevant prompting arrangements, whether for glaucoma and/or for other conditions and/or therapeutic events, may be equally suitable.

Figure 14:
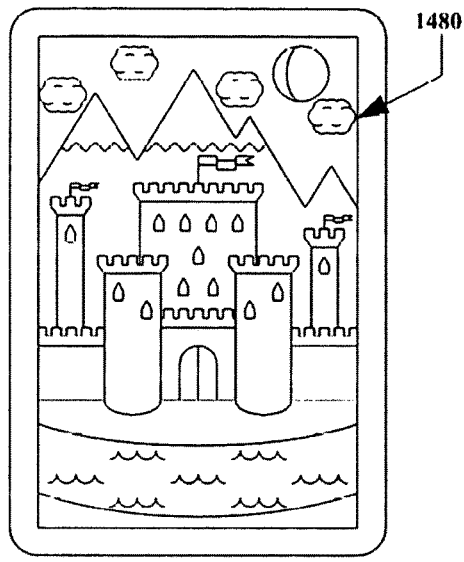
FIG. 14 through FIG. 17 show another example embodiment of a prompt according to the present invention.

For example, turning now to FIG. 14, therein another baseline image 1480 is shown, i.e. the image 1480 is without modification such as by a prompt according to the present invention.

Figure 15:
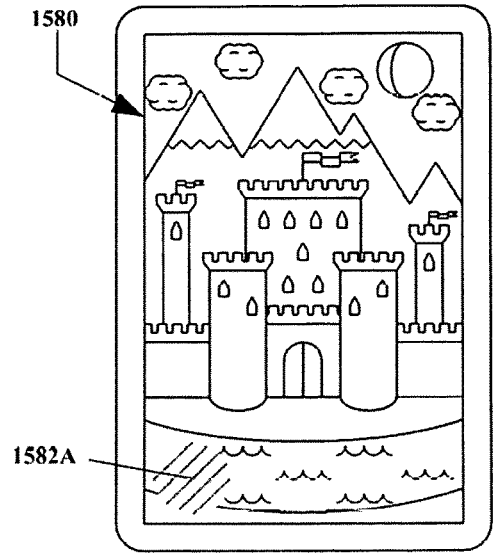

In FIG. 15, an image 1580 is shown that is at least somewhat similar to the image 1480 in FIG. 14. However, FIG. 15 also includes a prompting feature 1582A therein, obscuring a portion of the image 1580 in the periphery thereof.

Again with reference to glaucoma, in certain cases glaucoma manifests as discrete regions of lost and/or impaired sight, referred to as "scotomas" (singular "scotoma"). Scotomas associated with glaucoma typically appear in a subject's peripheral vision first, potentially increasing in size, number, and/or severity, while also appearing in the central vision as well as the peripheral vision. The prompting feature 1582A, in obscuring a discrete portion of the periphery of the image 1580, thus is at least somewhat similar to and/or evocative of a scotoma as might manifest as an early symptom of glaucoma. Thus, the arrangement shown in FIG. 15 may be considered to represent prompting that is contextually relevant to a subject's glaucoma.

Figure 16:
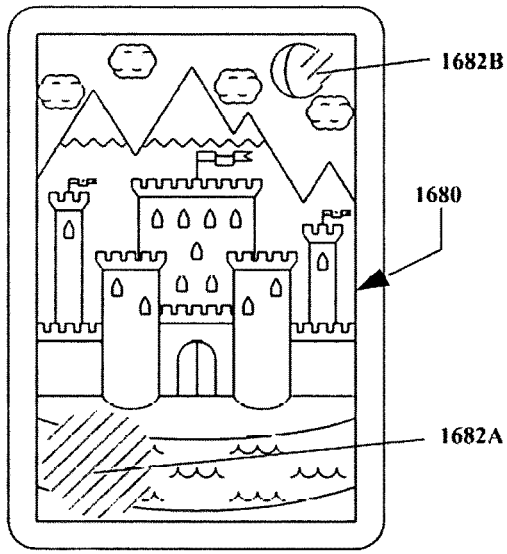

Turning now to FIG. 16, therein an image 1680 may be seen with prompting features 1682A and 1682B. The image 1680 and prompting feature 1682A may be seen to be at least somewhat similar to those in FIG. 15, however in FIG. 16 the prompting feature 1682A has increased in size, and a second prompting feature 1682B also has appeared, also in the periphery of the image 1680. A larger portion of the image 1680 is thus obscured by the prompting features 1682A and 1682B thus at least arguably being more noticeable and/or more readily attracting a subject's attention.

Figure 17:
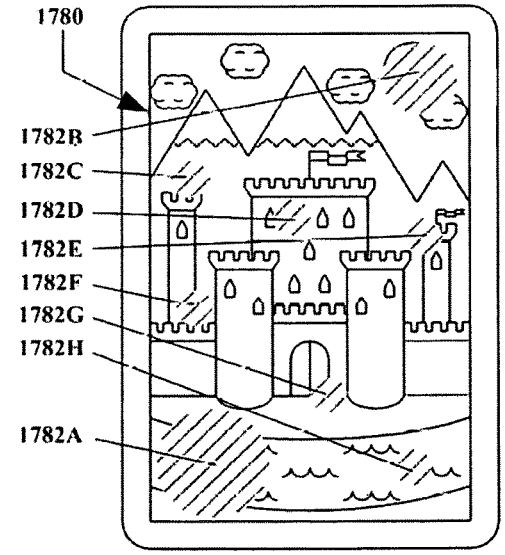

Similarly, in FIG. 17 therein an image 1780 may be seen with prompting features 1782A through 1782H. The image 1780 and prompting features 1782A and 1782B may be seen to be at least somewhat similar to those in FIG. 17, however in FIG. 17 prompting feature 1782B is larger. Also, new prompting features 1782C through 1782H also appear, both in the periphery of the image 1780 and also distributed throughout the central portion of the image 1780. Again, the prompting features 1782A through 1782H obscure a still larger portion of the image 1780, thus at least arguably being still more noticeable and/or still more readily attracting a subject's attention.

Considering FIG. 14 through FIG. 17 collectively as a time-sequence, it may be seen that the images shown therein are progressively obscured by the prompting features in a fashion resembling the progressive loss of eyesight associated with glaucoma. Thus, FIG. 14 through FIG. 17 may represent a prompting to a subject to administer a glaucoma medication, that prompting being contextually relevant at least insofar as the prompting to take the medication resembles the effect of the user not taking the medication, and/or the prompting is progressive as time passes (a feature that may also be contextually relevant, as glaucoma likewise typically is progressive in effect).

Figure 18:
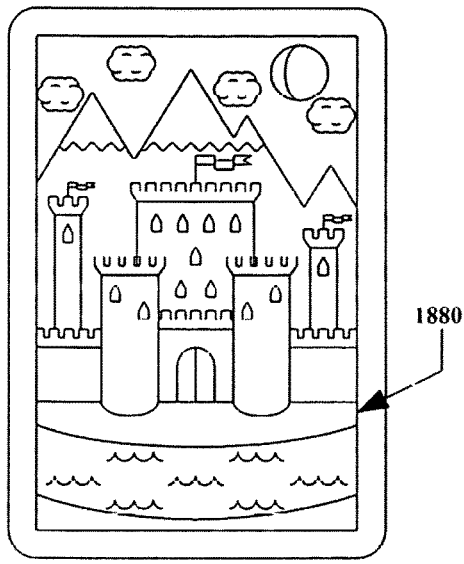
FIG. 18 through FIG. 21 show another example embodiment of a prompt according to the present invention.

Now with reference to FIG. 18, therein another baseline image 1880 is shown, i.e. the image 1880 is without modification such as by a prompt according to the present invention.

Figure 19:
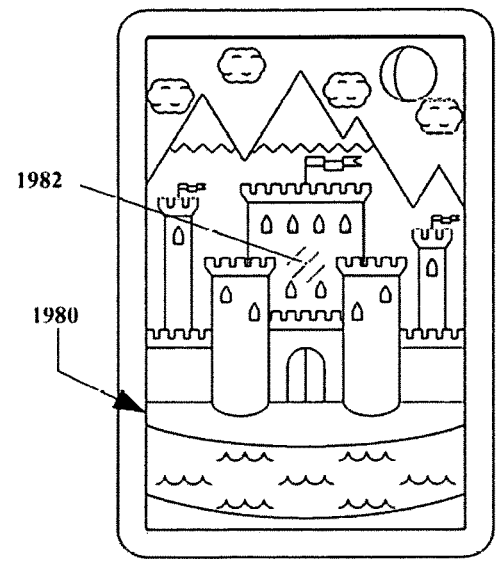

In FIG. 19, an image 1980 is shown that is at least somewhat similar to the image 1880 in FIG. 18. However, FIG. 19 also includes a prompting feature 1982 therein, obscuring a portion of the image 1980 near the center thereof.

Although certain previous figures have used glaucoma as an example, the present invention is not limited only thereto. Considering as an alternative example macular degeneration, in certain cases macular degeneration manifests as gradual loss and/or impairment of sight in the central vision (e.g. due to degeneration of the macula of the eye). Macular degeneration typically affects the central vision, with the area of impairment growing larger in size and/or the impairment becoming more pronounced. The prompting feature 1982, in obscuring a portion of the center of the image 1980, thus is at least somewhat similar to and/or evocative of an early manifestation of macular degeneration. Thus, the arrangement shown in FIG. 19 may be considered to represent prompting that is contextually relevant to a subject's macular degeneration.

Figure 20:
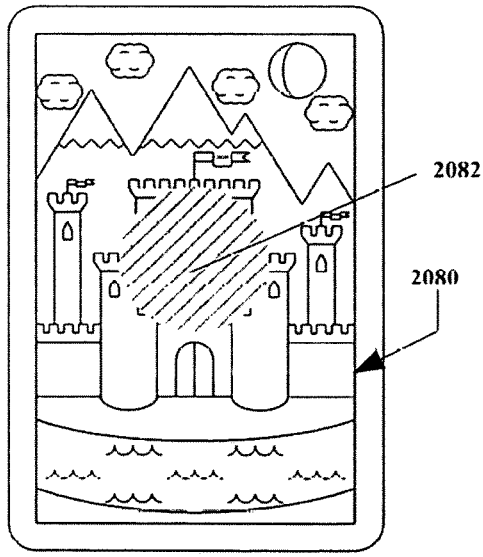

Turning now to FIG. 20, therein an image 2080 may be seen with prompting feature 2082. The image 2080 and prompting feature 2082 may be seen to be at least somewhat similar to those in FIG. 19, however in FIG. 20 the prompting feature 2082 has increased in size. A larger portion of the image 2080 is thus obscured by the prompting feature 2082 thus at least arguably being more noticeable and/or more readily attracting a subject's attention.

Figure 21:
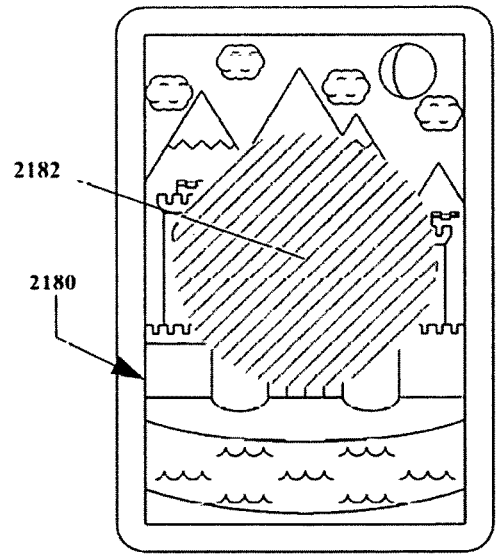

Similarly, in FIG. 21 an image 2180 may be seen with prompting feature 2182. The image 2180 and prompting feature 2182 may be seen to be at least somewhat similar to those in FIG. 20, however in FIG. 20 the prompting feature 2182 is larger. Again, the prompting feature 2182 obscures a still larger portion of the image 2180, thus at least arguably being still more noticeable and/or still more readily attracting a subject's attention.

Considering FIG. 18 through FIG. 21 collectively as a time-sequence, it may be seen that the images shown therein are progressively obscured by the prompting features in a fashion resembling the progressive loss of eyesight associated with macular degeneration. Thus, FIG. 18 through FIG. 21 may represent a prompting to a subject to administer a macular degeneration medication (or other therapy), that prompting being contextually relevant at least insofar as the prompting to take the medication resembles the effect of the user not taking the medication, and/or the prompting is progressive as time passes.

As has been stated, although certain examples herein reference eye conditions, the present invention is not limited only thereto. Now with reference to FIG. 22 therein another baseline image 2280 is shown, i.e. the image 2280 is without modification such as by a prompt according to the present invention.

Figure 22:
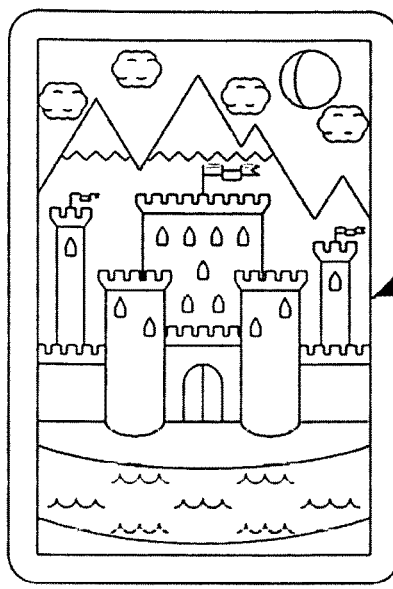
FIG. 22 through FIG. 25 show another example embodiment of a prompt according to the present invention.
Figure 23:
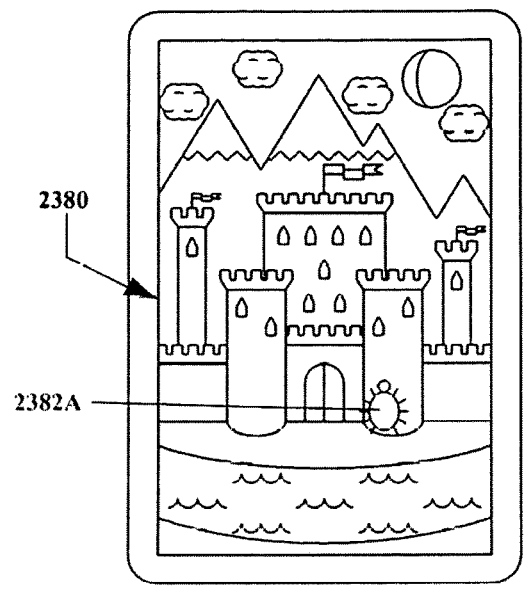

In FIG. 23, an image 2380 is shown that is at least somewhat similar to the image 2380 in FIG. 22. However, FIG. 23 also includes a prompting feature 2382A therein, obscuring a portion of the image 2380. The prompting feature 2382A is in the form of a graphic icon representing a stylized "bug", potentially being evocative for example of a bacterium, virus, etc.

Figure 24:
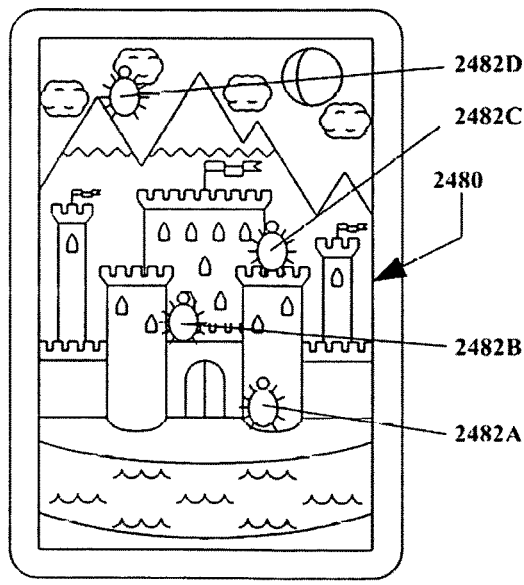

Turning to FIG. 24, therein an image 2480 may be seen with prompting feature 2482A. The image 2480 and prompting feature 2482A may be seen to be at least somewhat similar to those in FIG. 23, however in FIG. 24 additional prompting features 2482B, 2482C, and 2482D also are present. A larger portion of the image 2480 is thus obscured by the prompting features 2482A through 2482D, thus at least arguably being more noticeable and/or more readily attracting a subject's attention.

Figure 25:
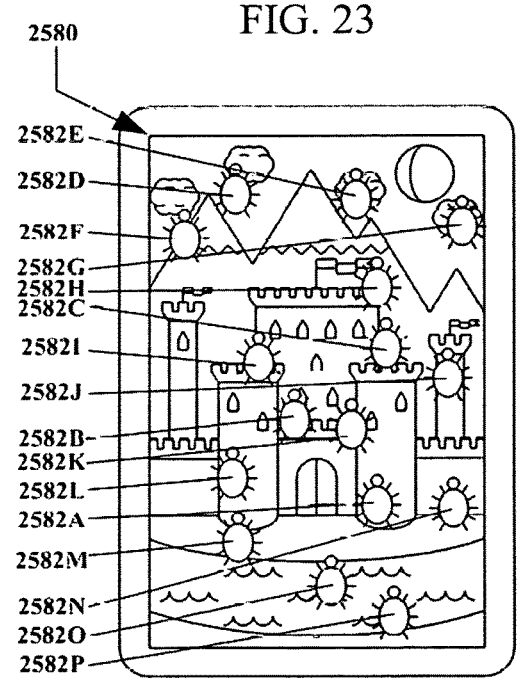

Continuing with FIG. 25, therein an image 2580 may be seen with prompting features 2582A through 2582D. The image 2580 and prompting features 2582A through 2582D may be seen to be at least somewhat similar to those in FIG. 24, however in FIG. 25 additional prompting features 2582E through 2582P also are present. A still larger portion of the image 2580 is thus obscured by the prompting features 2582A through 2582P, thus at least arguably being more noticeable and/or more readily attracting a subject's attention.

Considering FIG. 22 through FIG. 25 collectively as a time-sequence, it may be seen that the images shown therein are progressively obscured by the prompting features with increasing coverage of the images. The number of prompting features begins at one in FIG. 23, increases to four in FIG. 24 (doubling, then redoubling), and then increases to sixteen in FIG. 25 (again doubling and redoubling). Thus the number of prompting features increases geometrically, doubling twice between FIG. 23 and FIG. 24 and again doubling twice between FIG. 24 and FIG. 25.

It is noted that certain infectious organisms may typically increase in number geometrically, doubling over some period of time, redoubling again after a similar period of time, etc. Therefor FIG. 22 through FIG. 25 thus may resemble and/or evoke the progression of an infection, an arrangement that might be used as a prompt to a subject to administer an antibiotic medication, an antiviral medication, etc. in response to an infection. That prompting may be considered to be contextually relevant at least insofar as the prompting to take the medication may resemble the effect of the user not taking the medication (i.e. the infectious organisms may grow at a geometric rate), and/or the prompting may be progressive as time passes (with additional prompting features appearing over time).

It is emphasized that the arrangement shown in FIG. 22 through FIG. 25 is an example only, and that many variations are possible within the scope of the present invention. For example, even for an arrangement similar to that in FIG. 22 through FIG. 25, although two doublings are shown between FIG. 23 and FIG. 24 and between FIG. 24 and FIG. 25 the individual doublings might be presented instead (going from 1 to 2, 2 to 4, 4 to 8, etc.), or prompting features might appear individually but at a geometrically increasing rate, etc. An arrangement other than geometric growth likewise might be utilized.

While the prompting features shown in FIG. 22 through FIG. 25 are illustrated as static and motionless, prompting features that are animated and/or mobile, etc. also may be equally suitable. For example, individual "bugs" could appear as animations, moving about the screen, and so forth. Likewise, although the prompting features shown in FIG. 22 through FIG. 25 are shown as stylized, realistic icons showing some particular microorganism might be utilized instead. Other prompting features also might be suitable, including but not limited to images and/or representations of damage done by an infection.

Figure 26:
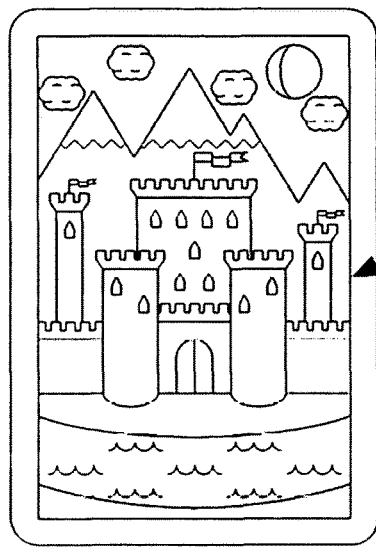
FIG. 26 through FIG. 29 show another example embodiment of a prompt according to the present invention.

As has been stated, although certain examples herein reference diseases treatable by medications, the present invention is not limited only thereto. Turning now to FIG. 26, therein another baseline image 2680 is shown, i.e. the image 2680 is without modification such as by a prompt according to the present invention.

Figure 27:
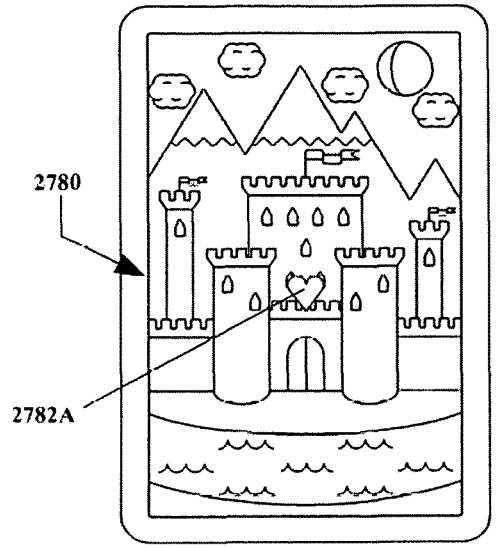

In FIG. 27, an image 2780 is shown that is at least somewhat similar to the image 2680 in FIG. 26. However, FIG. 27 also includes a prompting feature 2782 therein, obscuring a portion of the image 2780. The prompting feature 2782 is in the form of a graphic icon representing a stylized heart. Such an icon might be adapted, for example, to prompt a subject to engage in aerobic exercise, e.g. as part of a regular program of such exercise for maintaining cardiovascular health. The prompting feature 2782 thus may be considered to represent prompting that is contextually relevant to a subject's heart and/or heart health.

Figure 28:
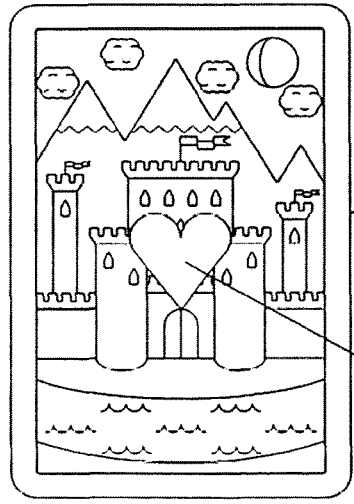

Turning now to FIG. 28, therein an image 2880 may be seen with a prompting feature 2882. The image 2880 and prompting feature 2882A may be seen to be at least somewhat similar to those in FIG. 27, however in FIG. 28 the prompting feature 2882 has increased in size. A larger portion of the image 2880 is thus obscured by the prompting feature 2882 thus at least arguably being more noticeable and/or more readily attracting a subject's attention.

Figure 29:
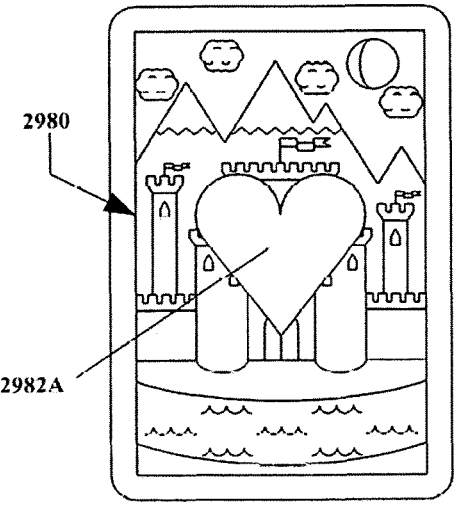

Similarly, in FIG. 29 therein an image 2980 may be seen with prompting feature 2982. The image 2980 and prompting feature 2982 may be seen to be at least somewhat similar to those in FIG. 28, however in FIG. 29 the prompting feature 2982 is larger. Again, the prompting feature 2982 is more prominent and obscures a still larger portion of the image 2980, thus at least arguably being still more noticeable and/or still more readily attracting a subject's attention.

Considering FIG. 26 through FIG. 29 collectively as a time-sequence, it may be seen that the images shown therein are progressively obscured by the prompting feature, the prompting feature becoming more prominent and obscuring more of the image over time. Thus, FIG. 26 through FIG. 29 may represent a prompting to a subject to engage in aerobic exercise, administer a glaucoma medication, that prompting being contextually relevant at least insofar as the prompting to exercise makes the device displaying the image decreasingly functional (as a subject's heart, body, etc. likewise may become decreasingly functional due to lack of regular aerobic exercise, etc.).

Although FIG. 10 through FIG. 29 show examples of contextually relevant prompting, the present invention is not limited only to the examples shown, nor is the present invention limited only to contextually relevant prompting. Other arrangements may be equally suitable.

Figures 30, 31:
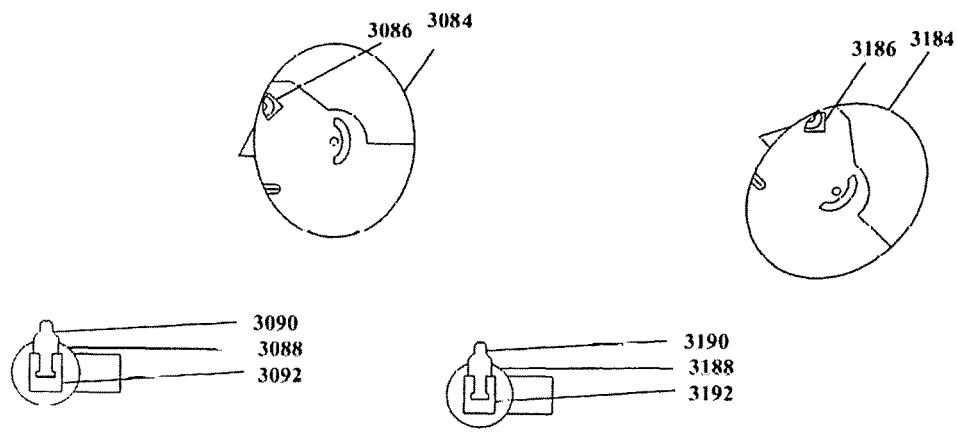

As has been disclosed, with regard to confirmation the present invention may utilize confirmation that is automatic, including but not limited to automatic confirmation gathering information from sensors. With reference now to FIG. 30, an example arrangement for automatic confirmation is shown beginning therein. It will be understood that, at least for the arrangement shown (and for certain other such arrangements shown herein), the example arrangement for automatic confirmation also may be viewed as an arrangement for sensing execution of a therapeutic event.

In FIG. 30, a stylized side view of a subject's head 3084 is shown, as well as a subject's hand 3088. FIG. 30 also shows one of the subject's eyes 3086, a medication container 3090 illustrated in the form of a squeeze bottle as might be utilized to administer medication in the form of eye drops. A sleeve 3092 also is illustrated disposed on the medication container 3090, the sleeve for example potentially serving as a platform for sensors and/or other elements supporting an implementation of the present invention.

As will be shown, certain therapeutic events—including but not limited to the administration of a medication in the form of an eye drop—may include therein motions and/or other actions sufficiently characteristic as to enable confirmation of those therapeutic events by sensing of those motions/actions. In FIG. 30, an early state of such a characteristic motion is shown, with the container 3090 held in front of the subject.

Moving on to FIG. 31, therein the user's head 3184 has tilted back, for example so as to elevate the eye 3186 to receive an eye drop. The hand 3188, and container 3190 with the sleeve 3192 thereon remain substantially as in FIG. 30.

Figures 32, 33:
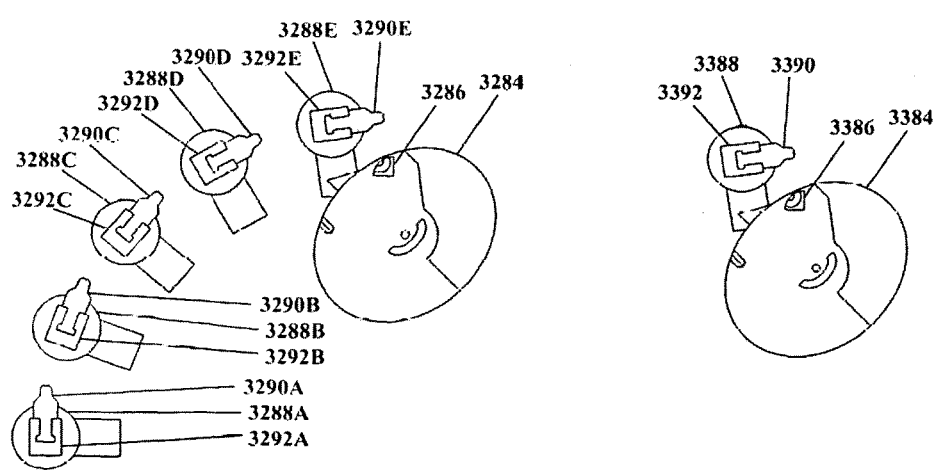

Turning to FIG. 32, a progression of positions are shown for the hand 3288 as the hand 3288 is raised to a position above the head 3284. Initially the hand 3288A begins in a low position, elevating progressively 3288B, 3288C, 3288D, until the uppermost position shown for hand 3288E. Similarly, the container and sleeve move from 3290A and 3292A, 3290B and 3292B, 3290C and 3292C, 3290D and 3292D, until the uppermost position shown for the container 3290E and the sleeve 3292E.

In FIG. 33, the subject's hand 3388 is shown elevated, substantially as in FIG. 32, with the container 3390 and sleeve 3392 gripped therein. The subject's head 3384 remains leaned back, with the eye 3386 positioned to receive the medication.

Now with reference to FIG. 34, the subject's head 3484 remains leaned back, with the eye 3486 positioned to receive the medication. The hand 3488 has rotated to tilt the container 3490 to dispense medication with the sleeve 3492 tilting as well.

In FIG. 35, the subject's hand 3588 has squeezed the container 3590 (and in the case shown also has squeezed the sleeve 3592, though a squeezable sleeve is not required). A drop of medication 3594 has been squeezed from the bottle 3590, and with the head 3584 tilted back the medication 3594 is positioned to fall into the subject's eye 3586.

Considering FIG. 30 through FIG. 35 collectively, a series of motions is apparent therefrom. A medication container—with a sensor sleeve thereon—is raised along an arc to a position above the subject's head, then inclined over the eye, then squeezed to administer the medication. Such a sequence of motions may, for at least certain embodiments of the present invention, be sufficiently characteristic as to be recognizable as a therapeutic act (in the example shown, administration of a medicated eye drop) as to enable confirmation of that therapeutic act by sensing those motions.

For example, as noted the sleeve may have sensors disposed therein and/or thereon. As a more concrete example, an arrangement of one or more accelerometers might detect the translation of the container along an arc, an arrangement of one or more gyroscopes might detect rotation of the container above the eye, and/or an arrangement of one or more pressure or flexure sensors might detect the squeezing of the container to dispense the medication.

A range of accelerometers, gyroscopes, pressure sensors, etc. may be suitable for use with the present invention, and the present invention is not particularly limited with regard thereto.

Moreover, other sensors besides those referenced above may be equally suitable. For example, image sensors might capture characteristic motions (and/or recognize those motions) and/or might capture characteristic objects such as a medication container. Alternatively, a microphone might capture sounds characteristic of administering asthma medication through an inhaler, a pulse sensor might record a change in pulse rate associated with aerobic activity, etc. The present invention is not particularly limited with regard to what phenomena may be sensed, and/or what sensors may be utilized therefor (if any).

Although in the example of FIG. 30 through FIG. 35 sensors are incorporated in a sleeve which is disposed on a medication container, it is emphasized that such an arrangement is not required, and the present invention is not limited thereto. Sensors may be distal to a medication bottle or other instrument associated with a therapeutic event. As previously noted, imagers may be utilized as sensors, and such imagers might be placed at some distance from the subject, for example imagers on smart phones, tablets, laptop computers, game consoles, security systems, etc. might be so utilized.

Furthermore, even if a characteristic motion is to be captured by sensing motions of a medication bottle and/or other implement of a therapeutic event, sensors are not required to be in contact or necessarily in proximity with such instrument.

With reference now to FIG. 36, a stylized side view of a subject's head 3684 is shown, as well as a subject's hand 3688. FIG. 36 also shows one of the subject's eyes 3686, a medication container 3690 illustrated in the form of a squeeze bottle as might be utilized to administer medication in the form of eye drops. A wristband 3696 also is illustrated disposed inward of the subject's hand 3688. The wristband 3696 may for example serve as a platform for sensors and/or other elements supporting an implementation of the present invention.

As has been described, certain therapeutic events, including but not limited to the administration of a medication in the form of an eye drop, may include therein motions and/or other actions sufficiently characteristic as to enable confirmation of those therapeutic events by sensing of those motions/actions. In FIG. 36, an early state of such a characteristic motion is shown, with the container 3690 held in front of the subject.

Moving on to FIG. 37, therein the user's head 3784 has tilted back, for example so as to elevate the eye 3786 to receive an eye drop. The hand 3788, container 3790, and wristband 3796 remain substantially as in FIG. 36.

Turning to FIG. 38, a progression of positions are shown for the hand 3888 as the hand 3888 is raised to a position above the head 3884. Initially the hand 3888A begins in a low position, elevating progressively 3888B, 3888C, 3888D, until the uppermost position shown for hand 3888E. Similarly, the container and wristband move from 3890A and 3896A, 3890B and 3896B, 3890C and 3896C, 3890D and 3896D, until the uppermost position shown for the container 3890E and the wristband 3896E.

In FIG. 39, the subject's hand 3988 is shown elevated, substantially as in FIG. 32, with the container 3990 and wristband 3996 gripped therein. The subject's head 3984 remains leaned back, with the eye 3986 positioned to receive the medication.

Now with reference to FIG. 40, the subject's head 4084 remains leaned back, with the eye 4086 positioned to receive the medication. The hand 4088 has rotated to tilt the container 4090 to dispense medication with the wristband 4096 moving as the hand 4088 rotates.

In FIG. 41, the subject's hand 4188 has squeezed the container 4190, potentially manipulating the wristband 4196 (e.g. via movement of muscles and tendons in the wrist as the container 4190 is squeezed). A drop of medication 4194 has been squeezed from the bottle 4190, and with the head 4184 tilted back the medication 4194 is positioned to fall into the subject's eye 4186.

Considering FIG. 36 through FIG. 41 collectively, a series of motions is apparent therefrom, at least somewhat similar to those shown and described with regard to FIG. 30 through FIG. 35. A medication container held in a hand—with a sensored wristband (e.g. a smartwatch, athletic wristband, health monitoring wristband, etc.) on the wrist below the hand—is raised along an arc to a position above the subject's head, then inclined over the eye, then squeezed to administer the medication. Such a sequence of motions may, for at least certain embodiments of the present invention, be sufficiently characteristic as to be recognizable as a therapeutic act (in the example shown, administration of a medicated eye drop) as to enable confirmation of that therapeutic act by sensing those motions.

For example, as noted the wristband may have sensors disposed therein and/or thereon. As a more concrete example, an arrangement of one or more accelerometers might detect the translation of the container along an arc, an arrangement of one or more gyroscopes might detect rotation of the container above the eye, and/or an arrangement of one or more pressure or flexure sensors might detect the squeezing of the container to dispense the medication. Sensors on wristbands may be adapted to determine a wide range of parameters, including certain factors that may be considered non-intuitive, such as waking body posture and/or sleep posture, even if sensors on such a wristband only directly sense the position and/or manipulation of the wrist and hand. For example, the position and/or manipulation of a wrist or hand may be indicative of an overall posture and/or body motion, such perhaps being determined through kinematic analysis.

As has been noted previously, a therapeutic event according to the present invention may include collecting data, including but not limited to health data regarding a patient or other subject. Although certain examples of therapeutic events have been described herein with regard to administering medication, using a medical device, etc. it is emphasized that the present invention is not limited only thereto.

Notably, the present invention is not limited only to discrete or "single point" therapeutic events. That is, a therapeutic event may constitute a sequence of health measurements distributed over time, position, etc. (potentially but not necessarily prompted by changes in time, position, etc.), and/or some other long-term and/or ongoing series or continuum of action. Likewise, a therapeutic event may include transmission of such collected data.

As a more concrete example, a therapeutic event might include the collection of data regarding when and how a subject takes a prescribed medication for blood pressure (for example), what the subject's blood pressure is at intervals and/or at specific times (e.g. "8 AM", or "when the subject wakes up"), potentially over a period of many days or months. Such a therapeutic event might also include environmental information regarding temperature, humidity, etc., other information regarding the subject such as where the subject is, what posture the subject is, what the subject is doing (sleeping, sitting, walking, running, etc.), and so forth.

Moreover, the present invention is not limited only to executing such actions subsequent to and/or in response to a prompt. That is, an embodiment of the present invention might record health data over a long period before or without a prompt, and then as a response to the prompt execute a therapeutic event in the form of transmitting the collected information to a database.

Thus, depending on the embodiment, a therapeutic event might constitute data collection, might constitute transmission of such data, etc. Likewise, a prompt is able to be a command to execute such data collection, is able to be a command to transmit a collection of such data to some other subject such as a database.

Both data collection as described, and other functions and structures of the present invention may be implemented either partially or entirely as executable instructions either already instantiated on a processor or instantiated thereupon, e.g. from a data store such as a hard drive, solid state drive, etc. The terms "may" and "might" used throughout the present disclosure are able to be replaced with "is/are able to" and "can."

The methods and devices disclosed herein is able to be utilized in administering a medication or facilitate the utilization of a medical device. In operation, a therapeutic event is established, one or more predetermined conditions are established, triggers are established, verification whether the trigger is presented is checked, and prompt is executed.

The above specification, examples, and data provide a complete description of the manufacture and use of the composition of the invention. Since many embodiments of the invention can be made without departing from the spirit and scope of the invention, the invention resides in the claims hereinafter appended.

I claim:

1. A machine-implemented method, comprising:

instantiating a definition for administering a medication in a processor;

instantiating a definition for a prompt for administering said medication in said processor, said prompt comprising graphical interference with a graphical user interface in communication with said processor and being adapted to evoke at least a portion of a medical effect associated with not administering said medication;

instantiating a definition for a trigger for delivering said prompt, said trigger comprising a status of a condition comprising at least one of a time, bioinformation for a subject for said medication, an identity of said subject, an action of said subject, and an environmental feature;

acquiring container sensor data in said processor regarding a change to said container from sensors engaged with said container, with sufficient resolution to resolve whether said change corresponds with administering said medication;

acquiring condition sensor data in said processor regarding said condition;

determining in said processor whether said medication has been administered from container sensor data;

determining in said processor whether said trigger is satisfied from said condition sensor data; and responsive to said trigger being satisfied and said medication not being determined to have been administered, delivering said prompt to said subject via said graphical user interface so as to impede a functional interaction of said processor with a user via said graphical user interface.

2. The method of claim 1, wherein:
determining whether said trigger is satisfied comprises at least one of a group consisting of determining a time, sensing a status of said subject, sensing bioinformation regarding said subject, and sensing said condition using a portable electronic device.

3. The method of claim 1, wherein:
said prompt comprises at least one of a group consisting of a text message, a telltale light, a visual image, an animation, and a change in video output.

4. The method of claim 1, wherein:
said prompt comprises obscuring at least a portion of a display visible to said subject.

5. The method of claim 4, comprising:
progressively obscuring said display, such that said portion thereof increases over time.

6. The method of claim 1, wherein:
said prompt comprises obscuring at least a portion of a display visible to said subject, said obscuring initiating in a periphery of said display, said obscuring progressing over time so as to increase said portion, said obscuring progressing such that said portion expands substantially toward a center of said display.

7. The method of claim 1, wherein:
said prompt comprises obscuring at least a portion of a display visible to said subject, said obscuring initiating proximate a center of said display, said obscuring progressing over time so as to increase said portion, said obscuring progressing such that said portion expands substantially away from a center of said display.

8. The method of claim 1, wherein:
said prompt comprises obscuring at least a portion of a display visible to said subject with at least one icon, said icon comprising a representation of a microorganism, a number of said at least one icon increasing over time so as to increase said portion.

9. The method of claim 1, wherein:
said prompt is contextually relevant.

10. The method of claim 1, comprising:
delivering said prompt via at least one of a group consisting of a portable electronic device, a wearable electronic device, a smart phone, a personal data assistant, a tablet, a smart watch, a head mounted display, a laptop computer, and a desktop computer.

11. The method of claim 1, wherein:
delivering said prompt comprises altering an output of a visual display.

12. The method of claim 11, wherein:
delivering said prompt comprises altering said output of said visual display in a manner substantially corresponding with an effect associated with not executing administering said medication.

13. The method of claim 12, wherein:
said prompt comprises an advisory, said prompt comprising at least one of a health advisory, information regarding an environmental factor, and an instruction.

14. The method of claim 1, wherein:
said prompt comprises an instruction to administer said medication.

15. The method of claim 1, comprising:
establishing at least one confirmation of administering said medication;
responsive to said medication being administered, executing said confirmation of administering said medication.

16. The method of claim 15, wherein:
said confirmation comprises at least one of a group consisting of an auditory signal, a visual signal, a tactile signal, a verbal message, a tone, a musical sequence, a text message, a vibration, a telltale light, a visual image, an animation, a change in audio output, a change in video output, and generating a data entry.

17. The method of claim 16, wherein:
said confirmation comprises a time of administering said medication.

18. The method of claim 16, comprising:
said confirmation comprises recording a data entry on a data store disposed in at least one of a group consisting of a medication dispenser, a medical device, a PDA, a smart phone, a smart watch, a head mounted display, a tablet, a laptop computer, and a desktop computer.

19. The method of claim 15, comprising:
delivering said confirmation to at least one of a group consisting of said subject for said medication and a second subject.

20. The method of claim 15, comprising:
delivering said confirmation to at least one of a group consisting of a caregiver, a portable electronic device, a smart phone, a personal data assistant, a tablet, a smart watch, a head mounted display, a laptop computer, a desktop computer, a health professional, emergency services, and a data store.

21. The method of claim 1, comprising:
said prompt is adapted to graphically resemble at least a portion of said medical effect associated with not administering said medication.

22. The method of claim 1, comprising:
said prompt is adapted to progressively interfere with said graphical user interface, such that said graphical interference increases over time.

23. The method of claim 1, comprising:
in response to said medication being determined to have been administered, recording that said medication has been administered and a medication time thereof.

24. A machine implemented method, comprising:
instantiating a definition for administering a medication in a processor;
instantiating a definition for a prompt for administering said medication in said processor, said prompt comprising graphical interference with a graphical user interface in communication with said processor and being adapted to evoke at least a portion of a medical effect associated with not administering said medication;

instantiating a definition for a trigger for delivering said prompt, said trigger comprising a status of a condition comprising at least one of a time, bioinformation for a subject for said medication, an identity of said subject, an action of said subject, and an environmental feature;

acquiring motion sensor data in said processor regarding a motion of said container from motion sensors, with sufficient resolution to resolve whether said a motion corresponds with administering said medication;

acquiring condition sensor data in said processor regarding said condition;

determining in said processor whether said medication has been administered from whether said motion sensor data corresponds with a motion of said container in administering said medication;

determining in said processor whether said trigger is satisfied from said condition sensor data;

responsive to said trigger being satisfied and said medication not being determined to have been administered, delivering said prompt to said subject via said graphical user interface so as to impede a functional interaction of said processor with a user via said graphical user interface.

25. The method of claim 24, wherein:
acquiring container sensor data comprises receiving data from at least one of a group consisting of an imager, an accelerometer, a gyroscope, and a pressure sensor.

26. The method of claim 24, wherein:
determining whether said medication is administered comprises sensing a manipulation of medication container other than motion.

27. The method of claim 26, wherein:
sensing said manipulation of said medication container comprises at least one of a group consisting of:
  receiving data from at least one sensor proximate said medication container;
  receiving data from at least one sensor distal to said medication container;
  visually sensing at least a portion of said medication container; and
  visually sensing a target on said medication container.

28. The method of claim 26, wherein:
sensing said manipulation of said medication container comprises visually sensing a target on said medication dispenser, said target comprising at least one of a group consisting of a bar code, a QR code, a static LED, a color-modulated LED, and an intensity-modulated LED.

29. The method of claim 24, wherein:
administering said medication comprises administering an eye drop.

30. The method of claim 24, comprising:
sensing said with a second sensor, said second sensor comprising at least one of a group consisting of:
  a sensor held in a hand of said subject;
  a sensor engaged with a wrist of said subject; and
  a sensor engaged with said medication container.

31. The method of claim 30 wherein:
said second sensor comprises at least one of a group consisting of an accelerometer, a gyroscope, and a pressure sensor.

32. The method of claim 31, wherein:
said medication container comprises an eyedrop bottle.

33. The method of claim 30, wherein:
said second sensor comprises a microphone disposed within said medication container.

34. The method of claim 33, wherein:
said medication container comprises an inhaler.

35. The method of claim 24, comprising:
said prompt is adapted to graphically resemble at least a portion of said medical effect associated with not administering said medication.

36. The method of claim 24, comprising:
said prompt is adapted to progressively interfere with said graphical user interface, such that said graphical interference increases over time.

37. The method of claim 24, comprising:
in response to said medication being determined to have been administered, recording that said medication has been administered and a medication time thereof.

38. A machine-implemented method, comprising:
instantiating a definition for administering an eye drop glaucoma medication in a processor of a smart phone;

instantiating a definition for a prompt for administering said medication in said processor, said prompt comprising graphical interference with a graphical user interface of said smart phone obscuring at least a portion of a display of said smart phone, initiating in a periphery of said display, progressing over time so as to increase said portion substantially toward a center of said display, so as to be evocative of a medical effect of glaucoma associated with an absence of administering said glaucoma medication;

instantiating a definition for a trigger for delivering said prompt, said trigger comprising a status of a condition comprising whether a current time is later than a planned time for administering said medication;

acquiring motion sensor data in said processor regarding a motion of said container from motion sensors engaged with said container, with sufficient resolution to resolve whether said motion of said container corresponds with administering said eye drop medication;

acquiring said current time in said processor for said condition;

determining in said processor whether said medication has been administered from said motion sensor data;

determining in said processor whether said trigger is satisfied from a comparison of said current time and said planned time;

responsive to said trigger being satisfied and said eye drop medication not being determined to have been administered, delivering said prompt to said subject via said graphical user interface so as to impede a functional interaction of said processor with a user via said graphical user interface; and responsive to said medication being determined to have been administered, storing that said medication has been administered and a medication time thereof.

39. An apparatus, comprising:
a processor;
a graphical prompter in communication with said processor;
a container sensor adapted to engage with a medication container and in communication with said processor, and adapted to sense a change to said container with sufficient resolution to resolve whether said change corresponds with administering said medication;
a condition sensor comprising at least one of a clock, a bioinformation sensor adapted to sense bioinformation for a subject of said medication, an identity sensor adapted to sense an identity of said subject, an action sensor adapted to sense an action of said subject, and an environment sensor adapted to sense an environmental feature, said at least one being in communication with said processor;
a definition for administering a medication instantiated on said processor;
a definition for a prompt for administering said medication instantiated on said processor, said prompt comprising graphical interference with a graphical user interface via said graphical prompter and being adapted to evoke at least a portion of a medical effect associated with not administering said medication;
a definition for a trigger for delivering said prompt, said trigger comprising a status of a condition comprising at least one of a time, bioinformation for a subject for said medication, an identity of said subject, an action of said subject, and an environmental feature;
executable instructions instantiated on said processor adapted for determining whether said medication has been administered from container sensor data from said container sensor;
executable instructions instantiated on said processor adapted to determine whether said trigger is satisfied from condition sensor data from said condition sensor; and
executable instructions instantiated on said processor adapted to deliver said prompt to said graphical prompter so as to impede a functional interaction of said processor with a user via said graphical user interface responsive to said trigger being satisfied and said medication not being determined to have been administered.

40. The apparatus of claim 39, wherein:
said processor is disposed in at least one of a group consisting of a medication container, a wrist device, a smart phone, a smart watch, a tablet, a pc, a television, and a set-top box.

41. The apparatus of claim 39, wherein:
said prompter comprises at least one of a group consisting of a display screen and an led.

42. The apparatus of claim 39, wherein:
said prompter is disposed in at least one of a group consisting of a medication container, a wrist device, a smart phone, a smart watch, a tablet, a pc, a television, and a set-top box.

43. The apparatus of claim 39, comprising:
an inputter, said inputter being adapted to receive at least one of a group consisting of a confirmation that said prompt is received and a confirmation that said medication is administered.

44. The apparatus of claim 39, further comprising:
executable instructions instantiated on said processor adapted to confirm a delivery of said prompt.

45. An apparatus, comprising:
a smart phone, comprising:
a processor;
a graphical display in communication with said processor;
a motion sensor adapted to engage with an eye drop medication container and in communication with said processor, and adapted to sense a motion of said container with sufficient resolution to resolve whether said motion corresponds with administering said medication;
a condition sensor comprising a clock in communication with said processor;
a definition for administering an eye drop glaucoma medication instantiated on said processor;
a definition for a prompt for administering said medication instantiated on said processor, said prompt comprising graphical interference with a graphical user interface in communication with said processor progressively obscuring at least a portion of said graphical display, initiating in a periphery of said display, progressing over time so as to increase said portion substantially toward a center of said display, so as to be evocative of a medical effect of glaucoma associated with an absence of administering said glaucoma medication;
a definition for a trigger for delivering said prompt, said trigger comprising a status of a condition comprising whether a current time is later than a planned time for administering said medication;
executable instructions instantiated on said processor adapted for determining whether a motion sensor data corresponds with a motion of said container in administering an eye drop of said medication;
executable instructions instantiated on said processor adapted to determine whether said trigger is satisfied from a comparison of said current time and said planned time;
executable instructions instantiated on said processor adapted to deliver said prompt to said display so as to impede a functional interaction of said processor with a user via said graphical user interface in response to said trigger being satisfied and said medication not being determined to have been administered;
executable instructions instantiated on said processor adapted to record that said medication has been administered and a medication time thereof in response to said medication being determined to have been administered.

46. The apparatus of claim 39, wherein:
said container sensor comprises a motion sensor.

47. The apparatus of claim 39, further comprising:
at least one of:
a pressure sensor adapted to sense a pressure on said container so as to resolve whether said pressure corresponds with administering said medication;
a microphone adapted to sense a sound proximate said container so as to resolve whether said sound corresponds with administering said medication;
an image sensor adapted to sense a motion of said container so as to resolve whether said motion corresponds with administering said medication; and
an image sensor adapted to sense characteristic objects so as to resolve whether said characteristic objects correspond with administering said medication.

48. The apparatus of claim 39, wherein:
said prompt is adapted to graphically resemble at least a portion of said medical effect associated with not administering said medication.

49. The method of claim 39, comprising:
said prompt is adapted to progressively interfere with said graphical user interface, such that said graphical interference increases over time.

50. The apparatus of claim 39, comprising:
executable instructions instantiated on said processor adapted to record that said medication has been administered and a medication time thereof in response to said medication being determined to have been administered.

51. An apparatus, comprising:
means for instantiating a definition for administering a medication in a processor;

means for instantiating a definition for a prompt for administering said medication in said processor, said prompt comprising graphical interference with a graphical user interface in communication with said processor;

means for instantiating a definition for a trigger for delivering said prompt, said trigger comprising a status of a condition comprising at least one of a time, bioinformation for a subject for said medication, an identity of said subject, an action of said subject, and an environmental feature;

means for acquiring container sensor data in said processor regarding a change to said container from sensors engaged with said container, with sufficient resolution to resolve whether said change corresponding with administering said medication;

means for acquiring condition sensor data in said processor regarding said condition;

means for determining in said processor whether said medication has been administered from container sensor data;

means for determining in said processor whether said trigger is satisfied from said condition sensor data; and means for delivering said prompt to said subject via said graphical user interface so as to impede a functional interaction of said processor with a user via said graphical user interface responsive to said trigger being satisfied and said medication not being determined to have been administered.

52. An apparatus, comprising:
means for instantiating a definition for administering a medication in a processor;
means for instantiating a definition for a prompt for administering said medication in said processor, said prompt comprising graphical interference with a graphical user interface in communication with said processor;
instantiating a definition for a trigger for delivering said prompt, said trigger comprising a status of a condition comprising at least one of a time, bioinformation for a subject for said medication, an identity of said subject, an action of said subject, and an environmental feature;
means for acquiring motion sensor data in said processor regarding a motion of said container from motion sensors, with sufficient resolution to resolve whether said a motion corresponds with administering said medication;
means for acquiring condition sensor data in said processor regarding said condition;
means for determining in said processor whether said medication has been administered from said motion sensor data;
means for determining in said processor whether said trigger is satisfied from said condition sensor data; and
responsive to said trigger being satisfied and said medication not being determined to have been administered, delivering said prompt to said subject via said graphical user interface so as to impede a functional interaction of said processor with a user via said graphical user interface.

53. An apparatus, comprising:
a processor;
a prompter in communication with said processor;
a motion sensor in communication with said processor, and adapted to sense a motion of said container with sufficient resolution to resolve whether said motion corresponds with administering said medication;
a condition sensor comprising at least one of a clock, a bioinformation sensor adapted to sense bioinformation for a subject of said medication, an identity sensor adapted to sense an identity of said subject, an action sensor adapted to sense an action of said subject, and an environment sensor adapted to sense an environmental feature, said at least one being in communication with said processor;
a definition for administering a medication instantiated on said processor;
a definition for a prompt for administering said medication instantiated on said processor, said prompt comprising graphical interference with a graphical user interface in communication with said processor and being adapted to evoke at least a portion of a medical effect associated with not administering said medication;
a definition for a trigger for delivering said prompt, said trigger comprising a status of a condition comprising at least one of a time, bioinformation for a subject for said medication, an identity of said subject, an action of said subject, and an environmental feature;
executable instructions instantiated on said processor adapted for determining whether said medication has been administered from motion sensor data from said motion sensor;
executable instructions instantiated on said processor adapted to determine whether said trigger is satisfied from condition sensor data from said condition sensor;
executable instructions instantiated on said processor adapted to deliver said prompt to said prompter so as to impede a functional interaction of said processor with a user via said graphical user interface in response to said trigger being satisfied and said medication not being determined to have been administered.

54. The apparatus of claim 53, wherein:
said condition sensor is disposed on at least one of a group consisting of a medication container, a wrist device, a smart phone, a smart watch, a tablet, a pc, a television, and a set-top box.

55. The apparatus of claim 39, wherein:
said sensor comprises at least one of a group consisting of an imager, a depth mapper, an accelerometer, a gyroscope, a pressure sensor, a code reader, and a microphone.

56. The apparatus of claim 53, further comprising:
at least one of:
a pressure sensor adapted to sense a pressure on said container so as to resolve whether said pressure corresponds with administering said medication;
a microphone adapted to sense a sound proximate said container so as to resolve whether said sound corresponds with administering said medication;
an image sensor adapted to sense a motion of said container so as to resolve whether said motion corresponds with administering said medication; and
an image sensor adapted to sense characteristic objects so as to resolve whether said characteristic objects correspond with administering said medication.

57. The apparatus of claim 53, wherein:
said prompt is adapted to graphically resemble at least a portion of said medical effect associated with not administering said medication.

58. The method of claim 53, comprising:
said prompt is adapted to progressively interfere with said graphical user interface, such that said graphical interference increases over time.

59. The apparatus of claim 53, comprising:
executable instructions instantiated on said processor adapted to record that said medication has been administered and a medication time thereof in response to said medication being determined to have been administered.

\* \* \* \* \*